(12) United States Patent
Sukumar et al.

(10) Patent No.: US 8,093,013 B2
(45) Date of Patent: Jan. 10, 2012

(54) CLAUDINS AS MARKERS FOR EARLY DETECTION, DIAGNOSIS, PROGNOSIS AND AS TARGETS OF THERAPY FOR BREAST AND METASTATIC BRAIN OR BONE CANCER

(75) Inventors: Saraswati V. Sukumar, Columbia, MD (US); Scott L. Kominsky, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 832 days.

(21) Appl. No.: 12/044,031

(22) Filed: Mar. 7, 2008

(65) Prior Publication Data

US 2009/0155278 A1 Jun. 18, 2009

(51) Int. Cl.
G01N 33/53 (2006.01)
G01N 33/567 (2006.01)
G01N 33/574 (2006.01)
G01N 33/48 (2006.01)

(52) U.S. Cl. ............. 435/7.23; 435/4; 435/7.1; 435/7.2; 435/7.21; 436/501; 436/503; 436/63; 436/64

(58) Field of Classification Search ................ 435/4, 7.1, 435/7.2, 7.21, 7.23; 436/501, 503, 63, 64
See application file for complete search history.

(56) References Cited

U.S. PATENT DOCUMENTS 7,033,473 B2 4/2006 Gascoyne et al.

FOREIGN PATENT DOCUMENTS

WO WO00/70349 11/2000

OTHER PUBLICATIONS

Hicks, et al am. J. Surg. Pathol. 30(9): 1097, 2006.*
Tokes, et al., Breast Cancer Research, 7: R296-R305, 2005.*
Ishikawa, et al, Cancer, 112(4):924-933, 2008, Abstract.*
Burmer, GC et al, 1991, Environmental Health perspectives, 93: 27-31.
Busken, C et al, Digestive Disease Week Abstracts and Itinerary Planner, 2003, abstract No. 850.
Hough et al (Cancer Res., 2000, 60:6281-6287).
http://en.wikipedia.org/wiki/Claudin, downloaded Sep. 4, 2007.
Weiner (Seminars Oncology, vol. 26, No. 4, 1999, pp. 41-50).
Kaiser (Science, 2006, 313:1370).
Internal Medicine, 4th Edition, Editor-in-chief Jay Stein, Elsevier Science, 1998 Chapters 71-72.
Montesano, R et al,1996, Intl J Cancer, 69(3): 225-235.

* cited by examiner

*Primary Examiner* — Alana Harris Dent
*Assistant Examiner* — Anne Holleran
(74) *Attorney, Agent, or Firm* — Whitham, Curtis, Christofferson & Cook, P.C.

(57) ABSTRACT

Methods of diagnosis, prognosis, and treatment of breast cancer, and of metastatic brain cancer, are provided The diagnostic and prognostic methods involve the immunohistochemical detection of the level of expression of the proteins claudin 1, 3, 4, and 7 in tissue or cell samples. Claudins 1 and 7 are underexpressed in the majority of breast cancers, and claudins 3 and 4 are overexpressed. The methods of treatment involve the use of *Clostridium perfringens* enterotoxin (or a variant thereof) to lyse metastatic cancer cells in the brain and bone that overexpress claudins 3 and 4.

3 Claims, 8 Drawing Sheets

CLAUDINS AS MARKERS FOR EARLY DETECTION, DIAGNOSIS, PROGNOSIS AND AS TARGETS OF THERAPY FOR BREAST AND METASTATIC BRAIN OR BONE CANCER

This invention was made using funds from grants from the Department of Defense having grant numbers DAMD17-01-0285 and DAMD17-02-1-0429. The United States government may have certain rights in this invention.

This application claims priority to international patent application PCT/US03/04371, filed Feb. 14, 2003, which in turn claims priority to U.S. provisional patent applications 60/356,860, filed Feb. 14, 2002 and 60/424,222, filed Nov. 6, 2002, the complete contents of which are hereby incorporated by reference.

BACKGROUND OF THE INVENTION

1. Field of the Invention

The invention generally relates to the diagnosis, prognosis, and treatment of cancer. In particular, the invention provides the use of claudin proteins as targets for detection and treatment of primary epithelial cancers and metastatic brain and bone cancer.

2. Background of the Invention

Breast cancer therapies have shown limited efficacy in patients with advanced disease making early diagnosis essential for long-term survival. Although many advances in diagnostic, prognostic, and therapeutic methods have been made over the last several years, breast cancer remains the second leading cause of cancer death in women and the leading cause of death in women between the ages of 40 and 55. Thus, there is an ongoing need for new and improved diagnostic, prognostic, and therapeutic techniques related to this disease.

Further, few effective therapies for metastatic brain or bone cancer are currently available, and there is an ongoing need for promising therapy for these diseases as well.

SUMMARY OF THE INVENTION

It is an object of this invention to provide methods of diagnosis, prognosis, and treatment of breast cancer, and of metastatic brain and bone cancer. The diagnostic and prognostic methods involve the immunohistochemical detection of the level of expression of the proteins claudin 1, 3, 4, and 7 in tissue or cell samples. Claudins 1 and 7 are underexpressed in the majority of breast cancers, and claudins 3 and 4 are overexpressed. The methods of treatment involve the use of *Clostridium perfringens* enterotoxin (or a variant thereof) or other cytotoxic agents targeted against claudins 3 and/or 4 to lyse cancer cells that express claudins 3 and 4.

The invention thus provides a method for diagnosing breast cancer or metastasis in a patient, comprising the steps of determining a level of expression of at least one claudin in a tissue or cell sample. In the method, the claudin may be claudin 1, claudin 3, claudin 4, or claudin 7. The second step of the method is to assess whether claudins 3 or 4 are expressed at a level which is higher than a predetermined level, or whether or not claudins 1 or 7 are expressed at a level which is lower than a predetermined level. Cancer or metastasis is implicated when claudins 3 or 4 are at or above the predetermined level, or when claudins 1 or 7 are at or below the predetermined level. The cancer of metastasis may be breast cancer, lung cancer, colon cancer, kidney cancer, prostate cancer, pancreas cancer, ovarian cancer, thyroid cancer, gastric cancer, head and neck cancer, and skin cancer. In one embodiment, the method is carried out by exposing the sample to at least one antibody to a claudin (for example, an antibody to claudins 1, 3, or 4, or any combination of these). The antibody may be directed to a C-terminal region of CLDN-7, for example, an antibody to SEQ ID NO. 1 (described below).

The method may further include the step of obtaining a sample of cells of interest from a patient, e.g. as a biopsy tissue sample or from ductal lavage fluid. In one embodiment of the invention, the claudins are claudins-3 or -4, or both, and said sample is blood.

The method may further comprise the step of determining a grade of a sample containing cells of interest. Such a determination is based on an assessment made in said assessing step, and wherein the tumor grade is low if staining for claudin-7 is high, or the tumor grade is high is staining for claudin-7 is low.

The present invention further provides a method of killing cancer cells that express claudins-3 or -4, or both claudins-3 and -4. The method comprises the step of exposing the cancer cells to molecules the recognize claudin-3 or claudin-4, and the molecules either kill the cancer cells or deliver cytotoxic agents that kill the cancer cells. In one embodiment of the invention, the molecules include *Clostridium perfringens* enterotoxin in sufficient quantities to lyse the cancer cells. The *Clostridium perfringens* enterotoxin may be truncated by 45 amino acids at the amino terminus, and may be encapsulated in vessels such as liposomes, biodegradable synthetic polymer wafers, or micro-spheres. In one embodiment, the *Clostridium perfringens* enterotoxin is part of a chimeric protein comprising a matrix metalloprotease that is overexpressed by breast tumors. In another embodiment, the molecules include antibodies that recognize claudin-3 or claudin-4, or both. The antibodies that recognize claudin-3 or claudin-4, or both may be attached to cytotoxic agent the kill cancer cells. In yet another embodiment, the cytotoxic agents may be contained within vessels such as liposomes, biodegradable synthetic polymer wafers, or micro-spheres. In another embodiment, antibodies that recognize claudin-3 or claudin-4 (or both) are attached to the vessels.

The cancer cells may be breast cancer cells, lung cancer cells, colon cancer cells, kidney cancer cells, prostate cancer cells, pancreas cancer cells, ovarian cancer cells, thyroid cancer cells, gastric cancer cells, head and neck cancer cells, and skin cancer cells. The cancer cells may be metastatic, and in some embodiments are located in a patient's brain or bone.

Rabbit anti-human Claudin-7 pAb was raised against the synthetic polypeptide (CKAGYRAPRSYPKSNSSKEYV) (SEQ ID NO:1), which corresponds to the C-terminus of human Claudin-7. The presence of Claudin-7 polyclonal antibody in rabbit sera was determined by ELISA. 96-well plates were coated over night with synthetic polypeptide at a concentration of 600 ng/50 ul. Plates were dried and incubated at room temperature (RT) in blocking buffer (50 g Milk/L PBS) for 2 hrs. Rabbit antisera was diluted in PBS, added to plate, and incubated for 2 hours at RT. Presence of Claudin-7 pAb was visualized using anti-rabbit secondary antibody conjugated to horse radish peroxidase (HRP) at 490 nm.

Figure 3A:
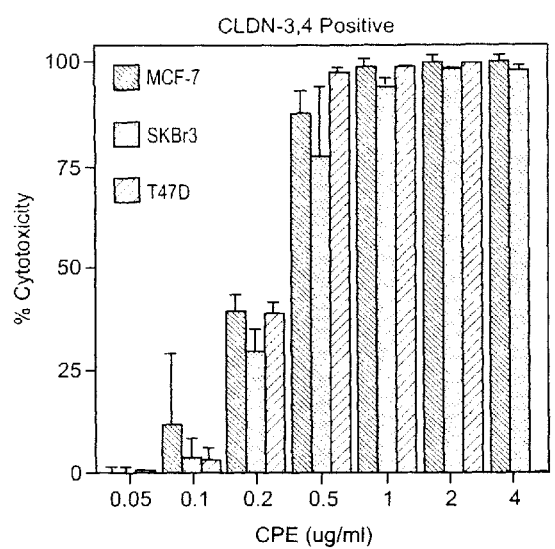

FIGS. 3A and B. *Clostridium perfringens* enterotoxin efficiently lyses human breast cancer cells expressing Claudins 3 and 4 while it has no effect on human breast cancer cells lacking Claudin 3 and 4 expression. Cells were plated at $3\times10^5$ cells/well in 6-well plates and grown to 80% confluence. Media was then removed and replaced with fresh media with or without CPE at concentration ranging from 0.05 to 4 ug/ml. Cells were incubated at 37° C. for 60 min. Floating and attached cells were collected and counted using a hemocytometer. Cell viability was determined by trypan blue (0.4%) dye exclusion. Data from representative experiments are expressed as % cytotoxicity as compared to media control −/−S.D. A, results from CLDN-3,4 positive cells; B, results from CLDN-3,4 negative cells.

FIGS. 4A and B. Treatment of T47D human breast cancer cell xenografts with *Clostridium perfringens* enterotoxin results in a reduction of tumor volume. T47D cells ($1\times10^7$) were resuspended in matrigel and subcutaneously injected bilaterally in the flank of 6-8 week old SCID mice. Tumors were grown to approximately 100 $mm^3$ prior to CPE treatment. CPE (A=2 ug, B=10 ug) was administered intratumorally on days 1, 3, 5, 7, 9, 11, and 13. Tumor volumes were measured using a caliper and reported +/−sd. Each experiment is representative of 6 animals. Reduction in CPE-treated tumor size (B) on day 14 relative to day 1 was found to be significant by Student's t-test (p=0.007).

FIG. 5. *Clostridium perfringens* enterotoxin efficiently lyses rat breast cancer cells (NMU 36/NMU 58) expressing Claudins 3 and 4 while it has no effect on NIH 3T3 cells lacking Claudin 3 and 4 expression. Cells were plated at $3\times10^5$ cells/well in 6-well plates and grown to 80% confluence. Media was then removed and replaced with fresh media with or without CPE at concentration ranging from 0.05 to 4 ug/ml. Cells were incubated at 37° C. for 60 min. Floating and attached cells were collected and counted using a hemocytometer. Cell viability was determined by trypan blue (0.4%) dye exclusion. Data from representative experiments are expressed as % cytotoxicity as compared to media control +/−S.D.

FIG. 6A-D. Recombinant CPE treatment of Sprague-Dawley NMU-induced breast tumor results in a reduction in tumor volume. Sprague-Dawley NMU-induced tumors were injected intraductally with (A, B) 17 ug CPE on days 1, 5, and 11 or (C, D) 30 ug CPE on days 1, 7, 9, 14, 16, 19, 22, and 26 versus PBS alone. Tumor volumes were measured using a caliper. Each graph is representative of 1 tumor.

FIG. 7. Intraductal administration of native CPE significantly inhibits the growth of NMU-induced rat mammary tumors. Female Sprague-Dawley rats (3-6 weeks old) were injected with 50 mg/kg NMU i.p. CPE was administered ID at 3 or 5μ/injection once every three days for 30 days once tumors grew to a size of 100 $mm^3$. Tumor size was measured using calipers three times per week. Significant differences in tumor size between CPE-treated and Control tumors was determined by Student's t-test.

FIG. 8. Intracranial administration of CPE significantly increases the survival of mice with established breast cancer metastasis to the brain. MDA-MB-468 human breast cancer cells were injected intracranially into athymic nude mice. Following the establishment of solid tumor, mice were administered intracranial injections of either 0.5 μg CPE or PBS three times per week for two weeks. Animals were observed for signs of neurological complications resulting from tumor burden and sacrificed when moribund.

DETAILED DESCRIPTION OF THE PREFERRED EMBODIMENTS OF THE INVENTION

The present invention provides diagnostic and prognostic methods for the detection of breast cancer. The methods are based on the discovery that certain tight junction proteins, namely claudins 1, 3, 4, and 7, are differentially expressed in breast cancer cells. In particular, claudins 1 and 7 are underexpressed in breast cancer cells and tissue, compared to normal breast cells and tissue, while claudins 3 and 4 are overexpressed in breast cancer cells and tissue, compared to normal breast cells and tissue. Thus, the detection of the expression (or lack thereof) of one or more of claudins 1, 3, 4 and 7 provides a means of determining whether or not cells or tissue from the breast are malignant. Such detection methods may be used, for example, for early diagnosis of the disease, to monitor the progress of the disease or the progress of treatment protocols, or to assess the grade of the cancer. The grade of the cancer is related to the progression of disease and thus aides in diagnosis, prognosis, and treatment considerations.

The detection of the expression profile of claudins 1, 3, 4 and/or 7 in breast cells may be carried out by any of several means well known to those of skill in the art. In a preferred embodiment of the present invention, the method of detecting claudins 1, 3, 4 and/or 7 is immunological in nature. By 'immunological', we mean that antibodies (e.g., monoclonal antibodies) specific for claudins 1, 3, 4 or 7, will be used. By "specific for claudins 1, 3, 4 or 7" we mean antibodies that recognize claudin 1, 3, 4, or 7 while not cross-reacting with samples containing other proteins.

The antibodies which can be used according to the method of the invention can be monoclonal antibodies prepared using hybridoma fusion techniques or can be derived from known secreting myeloma cell lines. Those of skill in the art will recognize that many techniques are available for the production of monoclonal antibodies.

While in a preferred embodiment of the present invention the method of detection of claudins is by utilizing monoclonal antibodies, those of skill in the art will recognize that other methods of detection can also be used in the practice of the invention. For example, polyclonal antibodies raised against a claudin (or fragment thereof) might also be used in various immuno assays. For example, in a preferred embodiment of the invention, for the detection of claudin 7, a polyclonal antibody against a synthetic polypeptide with the sequence CKAGYRAPRSYPKSNSSKEYV, (SEQ ID NO: 1) which corresponds to the C-terminus of human claudin-7 is used.

Many antibody detection systems are known to those of skill in the art and can be employed within the scope of the present invention. For example, the antibody may be diagnostically labeled. The term "diagnostically labeled" means that the antibody has attached to it a diagnostically detectable label. Many such labels and methods of conjugating labels to antibodies are well-known to those of skill in the art. Examples of types of labels which can be used in the practice of the present invention include but are not limited to fluorescent labels, enzyme labels, and radionuclide labels, specific binding pair components, colloidal dye substances, fluorochromes, reducing substances, latexes, digoxigenin, metals, particulates, dansyl lysine, antibodies, protein A, protein G, electron dense materials, chromophores and the like.

Any suitable label, whether directly or indirectly detectable, may be employed. One skilled in the art will recognize that these labels set forth above are merely illustrative of the different labels that could be utilized in this invention.

Many methods employing antibodies which specifically bind target substances are known in the art. Preferred methods include immunochemical methods, such as enzyme-linked immunosorbent assay (ELISA) methods, immunonophelometry methods, agglutination methods, precipitation methods, immunodiffusion methods, immunoelectrophoresis methods, immunofluorescent methods, and radioimmunoassay methods. Assays for detecting the presence of proteins and/or peptides with antibodies have been previously described and follow known formats, such as a standard blot and ELISA formats. These formats are normally based on incubating an antibody with a sample suspected of containing the protein or peptide and detecting the presence of a complex between the antibody and the protein or peptide. The antibody is labeled either before, during or after the incubation step.

Immobilization is usually required and may be accomplished by immobilizing the protein or peptide to a solid surface, such as a microtiter well, or by binding the protein to immobilized antibodies.

In a preferred embodiment, the claudin(s) is bound to an immobilized first antibody. A second labeled antibody, also specific for the claudin, or specific for the first antibody, is then bound, unbound material is washed away, and the complex is detectable due to the immobilized label of the second antibody. Such assays are well-known to those of skill in the art and include such assays as simultaneous sandwich, forward sandwich and reverse sandwich immunoassays, terms which are well-known to those of skill in the art.

Many solid phase immunoabsorbents for immobilization are known and can be used in the practice of the present invention. Well-known immunoabsorbents include beads formed from glass, polystyrene, polypropylene, dextran, nylon and other material; and tubes formed from or coated with such materials, and the like. The immobilized antibodies may be covalently or physically linked to the solid phase immunosorbent by techniques such as covalent bonding via an amide or ester linkage or by absorption.

In each of the above assays, the details of the assay protocol, such as time and temperature of incubation, may vary according to the concentration of antibodies used, the source and form of the sample, the affinity of the antibodies for their target molecules, etc. In a preferred embodiment of the present invention, an ELISA assay may be carried out as follows: 96-well microtiter plates are coated with a monoclonal first antibody specific for a claudin 1, 3, 4 and/or 7. The first antibody is immobilized in the wells. Standards and samples are pipetted into wells in, for example, duplicate or triplicate, and any claudin present in the standards and samples will be bound by the immobilized antibody. The standards are composed of known concentrations of claudin, which is known to be crossreactive with the first antibody. After incubation at room temperature for 2 hours, the wells are washed with an appropriate buffer to remove any unbound substances. Then a second enzyme-linked polyclonal (or monoclonal) antibody specific for claudin (or for the primary antibody) is added to the wells. After a 1 hour incubation at room temperature, the wells are again washed with an appropriate buffer to remove unbound antibody-enzyme reagent, and a solution which contains a substrate for the enzyme is added to the wells. The substrate is such that when it is acted on by the enzyme, a characteristic color is produced. Color will develop in proportion to the amount of enzyme present in the wells, which is directly proportional to the amount of bound claudin. After an appropriate period of time, the color development is stopped and the intensity of the color will be measured spectrophotometrically. The amount of claudin in the samples will be determined by comparing the color intensity of the sample wells to that of the control wells which contain a known amount of claudin.

The antibodies to be employed in the practice of the present invention are specific for claudin 1, 3, 4, and/or 7 and may be specific for any epitope of claudin 1, 3, 4, and/or 7. The antibodies may be raised against purified samples of a synthetic peptide having a sequence identical to that of claudin 1, 3, 4, and/or 7, either the full-length native form of the protein, or to proteolytic or synthetic fragments thereof. Those of skill in the art will readily recognize that there are numerous established protocols available for generating antibodies to specific peptides and proteins.

Various types of immuno assays which might be utilized in the practice of the present invention include but are not limited to immunoelectrophoresis, nephelometry, gel electrophoresis followed by Western blot, dot blots, affinity chromatography, immuno-fluorescence, and the like. In addition, other methods of detection of peptides known to those of skill in the art may be used in the practice of the current invention, such as gas chromatography/mass spectrometry, HPLC, and gel electrophoresis followed by sequencing.

In general, such methods involve obtaining a sample to be tested. Such samples may be obtained by any of many methods known to those of skill in the art. For example, the cells and/or tissue may be from a biopsy sample. More preferably, since the method is designed to detect breast cancer at very early stages, the sample may be ductal lavage fluid which may contain cells with altered claudin expression before a recognizable tumor mass has developed. Further, the sample may also be blood since the detection of claudins 3 and 4 in blood may be indicative of the presence of tumors or metastasis.

The sample of cells or tissue is prepared and exposed to the antibody or a mixture of antibodies according to means which are known to those of skill in the art. Briefly, tissue sample may be obtained by biopsy, lumpectomy, or mastectomy. Samples are then paraffin embedded and sectioned for immunohistochemical analysis of gene expression. cells may be obtained by ductal lavage and/or collection of blood. Red blood cells are then removed from whole blood by lysis in $H_2O$. Protein is then extracted from the remaining mixture of leukocytes and cancer cells or ductal lavage fluid. Equal amounts of protein are then absorbed to a 96-well plate over night for ELISA based assay. Alternatively, serum may be separated from blood samples. Proteins are then immobilized to a solid support for ELISA based assay.

The present invention further provides a kit for use in, for example, the screening, diagnosis or monitoring of breast cancer. Such a kit may comprise antibodies to claudins 1, 3, 4 and/or 7, a reaction container, various buffers, secondary antibodies, directions for use, and the like. In these kits, antibodies may be provided with means for binding to detectable marker moieties or substrate surfaces. Alternatively, the kits may include antibodies already bound to marker moieties or substrates. The kits may further include positive and/or negative control reagents as well as other reagents for carrying out diagnostic techniques. For example, kits containing antibody bound to multiwell microtiter plates can be provided. The kit may include a standard or multiple standard solutions containing a known concentrations of claudins or other proteins for calibration of the assays. A large number of control samples will be assayed to establish the threshold, mode and width of the distribution of claudins 1, 3, 4 and 7 in normal cells and tissues against which test samples will be compared. These data will be provided to users of the kit.

In general, in order to be considered significantly over expressed (i.e. to be considered "positive" for the presence of the claudin), a claudin will be detected as present or in an amount of about 10 to about 100% or more above the known, standardized level of normal control tissue, or more preferably from about 25 to about 100% or more above the known, standardized level of normal control tissue. In general, in order to be considered significantly under expressed, a claudin will be detected as present or in an amount of about 25 to about 75% or more below the known, standardized level of normal control tissue, or more preferably from about 50 to about 100% or more lower than the known, standardized level of normal control tissue. By "known, standardized level of normal control tissue" we mean that level detected in equivalent tissue derived from disease-free individuals. Further, such comparisons are typically made in comparison to a known negative control, such as tissue known to be devoid of the antigen being detected.

Other means of detecting the expression profile of claudins 1, 3, 4 and or 7 include but are not limited to, for example, detection of mRNA encoding one or more of the proteins. Those of skill in the art are well acquainted with methods of mRNA detection, e.g. via the use of complementary hybridizing primers (e.g. labeled with radioactivity or fluorescent dyes) with or without polymerase chain reaction (PCR) amplification of the detected products, followed by visualization of the detected mRNA via, for example, by electrophoresis (e.g gel or capillary); by mass spectroscopy; etc. Any means of detecting the presence of the mRNA in excess over a normal or baseline control (or to detect the absence of the mRNA compared to such a control) may be used in the practice of the present invention.

Further, in an assay designed to detect the expression profile or pattern of claudins 1, 3, 4 and/or 7, in breast cells or tissue, at least one but possibly two, three or all four of claudins 1, 3, 4 and 7 may be assayed. This may be true, for example, where the detection of claudin 7 is involved since it is expressed at very low levels or not at all in about 70% of breast carcinomas. Thus, advantages may accrue by assaying for claudin 7 together with one or more of the claudins simultaneously as a panel. Such a profile or panel may be designed according to guidelines which are well-known to those of skill in the art.

Since claudin 7 is expressed at very low levels or not at all in about 70% of breast carcinomas, it is possible that its reintroduction into breast cancer cells would impair the ability of breast cancer cells to metastasize. Thus, the invention also encompasses a method of preventing the metastasis of breast cancer cells by reintroducing claudin 7 into breast tumor cells, or alternatively, by inducing expression of claudin 7 in breast cancer cells. Means of carrying out this aspect of the invention are known to those of skill in the art. For example, a vector containing DNA encoding claudin 7 may be introduced into the breast cancer cells via gene therapy techniques. Alternatively, the claudin 7 protein may be introduced into the cells via tagging the claudin protein to a Trojan peptide (e.g. HOX proteins, TGF-β, etc.) or attaching claudin 7 to ligands or receptors expressed on breast cancer cells, etc. Administering there agents intraductally would confine the uptake to the breast epithelial cells lining the ducts, and tumors arising from these epithelia.

Claudins 3 and 4 are known to be overexpressed in breast cancer cells. Therefore, in yet another aspect, the present invention also provides targeted antibody and T-cell immunotherapy for breast cancer. Humanized monoclonal antibodies specific for claudin 3 and 4 are generated. These antibodies are administered systemically or locally. The binding of the antibody to cancer cells expression claudin 3 and 4 will result in cancer cell death by subsequent recognition and attack by cytotoxic T-cells or other immune cells participating in antibody dependent cell cytotoxicity (ADCC) reactions (e.g. natural killer cells, macrophages, etc.). Alternatively, cytotoxic molecules may be conjugated to claudin 3 and 4 antibodies allowing targeted delivery of cytotoxic compounds to the cancer cells. Examples of such cytotoxic agents include but are not limited to Doxil, *Pseudomonas exotoxin*, and paclitaxel. Additionally, claudin-3 and -4 antibodies can be attached to the exterior of vessels containing cytotoxic agents, which are designed for slow agent release, including liposomes and biodegradable synthetic polymer wafers or micro-spheres. Vaccines consisting of irradiated tumor cells overexpressing claudins, with or without augmentation with cytokines, could also result in the generation of T-cells that specifically recognize over-expressed claudins on tumor cells and cause cytotoxicity.

Claudins 3 and 4 are known to function as receptors for *Clostridium perfringens* enterotoxin (CPE). When cells which express claudins 3 and 4 are exposed to CPE, the toxin binds to the cells, induces formation of a pore in the cell membrane, and causes lysis of the cells. Because claudins 3 and 4 are expressed in epithelial cancer cells, CPE can be used to treat epithelial cancers. Exposure of epithelial cancer cells (e.g. breast cancer cells, prostate cancer cells, pancreas cancer cells, etc.) to CPE results in binding of the toxin to the cells, internalization and lysis of the cancer cells. In the case of breast cancer, the reduced sensitivity of normal mammary epithelial cells relative to breast cancer cells allows CPE to preferentially destroy breast cancer cells. In many cases, lysis will cause death of the cells. However, those of skill in the art will recognize that the method may still be valuable if all cells are not necessarily killed outright, but are damaged so as to slow their rate of replication and/or growth, or made more susceptible to other types of treatment such as radiation or chemotherapy. Further, it is understood that the methods of the present invention may be practiced in conjunction with other cancer treatment protocols such as radiation, chemotherapy, etc.

In one embodiment of the invention, the entire, native CPE toxin molecule (GenBank Accession #M98037) is utilized for the treatment of breast cancer. However, those of skill in the will recognize that the practice of the present invention need not be limited to the use of the entire native sequence. Several active forms or variants of CPE are known or can be designed by well-known, routine, genetic engineering techniques and can also be utilized in the practice of the present invention. For example, with respect to amino acid sequences, variants may exist or be constructed which display: conservative amino acid substitutions; non-conservative amino acid substitutions; truncation by, for example, deletion of amino acids at the amino or carboxy terminus, or internally within the molecule; or by addition of amino acids at the amino or carboxy terminus, or internally within the molecule (e.g. the addition of a histidine tag for purposes of facilitating protein isolation, the substitution of residues to alter solubility properties, the replacement of residues which comprise protease cleavage sites to eliminate cleavage and increase stability, the addition or elimination of glycosylation sites, and the like, or for any other reason). Such variants may be naturally occurring (e.g. as a result of natural variations between species or between individuals); or they may be purposefully introduced (e.g. in a laboratory setting using genetic engineering techniques). All such variants of the sequences disclosed herein are intended to be encompassed by the teaching of the present invention, provided the variant CPE retains the ability to bind to claudin 3 and 4 receptors, and to lyse the cell to which it binds. Preferably, amino acid sequence identity of such variants when compared to native CPE will be in the range of about 50 to about 100%, and more preferably in the range of about 75 to about 100%, and most preferably in the range of about 80 to about 100%. The identity is with reference to the portion of the amino acid sequence that corresponds to the original native sequence, i.e. not including additional elements that might be added, such as those described below for chimeric proteins. Further, such a variant will retain at least from about 50 to 100% or more of the ability to bind to claudins 3 and 4 and preferably will retain about 75 to 100% or more of the ability to bind to claudins 3 and 4. Further, such a variant will retain cell lysing activity of native CPE in the range of about 50 to 100% or more, or preferably in the range of about 75 to 100% or more. By "cell lysing activity" we mean the ability to initiate the production of pores in the cell membrane, leading to rupture and lysis of the cell, and typically cell death.

In a preferred embodiment of the invention, the CPE variant is one in which the N-terminal 45 amino acids of CPE have been removed to generate a CPE protein known to exhibit twice the cytotoxicity of native CPE. The use of a variant with enhanced cytotoxicity will allow an increased level of drug activity thereby increasing therapeutic efficacy at anatomical sites where injection volume is limiting (e.g. injection of solid tumors, brain, bone, etc.).

The invention also encompasses chimeric CPE toxin molecules, for example, CPE proteins comprised of native CPE (or a variant as described above) plus additional sequences which are not necessarily associated with CPE, but the addition of which conveys some additional benefit. For example, such benefit may have utility in isolation and purification of the protein, (e.g. histidine tag, GST, and maltose binding protein); or in directing the protein to a particular intracellular location (e.g. yeast secretory protein). All such chimeric constructs are intended to be encompassed by the present invention, provided the portion of such construct that is based on CPE is present in at least the indicated level of homology. In a preferred embodiment, CPE will be linked to a macromolecule (e.g. a protein, or a polypeptide) that is expressed exclusively by malignant epithelial cells or tissue in order to more specifically target epithelial cancer cells and allow for systemic delivery of the CPE. Examples of such macromolecules include but are not limited to: proteases such as matrix metalloproteases which are known to be over-expressed by various epithelial tumors; breast tumor-associated stromal elements, breast tumor vasculature, etc.

For the purposes of treating breast cancer, delivery of the CPE or CPE variant can be carried out by any suitable means, many of which are known to those of skill in the art. Because some non-cancerous cells also express claudin 3 and 4, in preferred embodiments of the invention, the CPE is delivered directly to the site of a tumor to avoid systemic lysis of otherwise healthy tissue. Examples of methods of direct delivery include but are not limited to direct injection into a tumor bed, topical application, and the like. In a preferred embodiment of the invention, delivery to breast tumors will be intraductal, for example, as described in U.S. Pat. No. 6,330,472 (Sukumar et al., issued Dec. 11, 2001), the entire contents of which is hereby incorporated by reference. The CPE may be delivered in any suitable form, many of which are known to those of skill in the art. For example, the CPE may be contained within vessels including but not limited to liposomes and biodegradable synthetic polymer wafers or micro-spheres designed for slow drug release.

The invention further encompasses the treatment of metastasized cancer which has metastasized to any site in the body. In one embodiment of the invention, the metastasis is located in the brain and, or the bone. It is well-recognized that patients afflicted with breast, lung, colon, kidney, prostate, pancreas, and skin cancer frequently die from neurological complications resulting from metastases to the brain or bone, or both. Most carcinomas express claudins 3 and 4 (e.g. breast, lung, colon, kidney, prostate, pancreas, etc.) whereas the cell types of the brain and bone do not. Thus, intracranial or intraosteal administration of CPE may be used to eliminate cancer cells or tumors, especially metastatic tumors originating from these sources while leaving non-malignant brain and bone cells unharmed. In other words, targeting claudins 3 and 4 with CPE may provide a means of eliminating metastatic cancer from the brain and bone without damaging the brain itself. Drug delivery may be accomplished by any of several means which are well known to those of skill in the art, including but not limited to stereotactic injection, implantation of drug saturated wafers, micropump, etc.

Those of skill in the art will recognize that the amount of CPE which must be administered in order to treat primary epithelial cancer and cancer metastases will vary from case to case depending on several factors (e.g. the size, gender, age and general health of the patient, the stage of the disease, etc) and is best determined by a skilled practitioner such as a physician. The details of the dosage are typically determined during clinical trials. However, in general, the quantity to be administered will be in the range of from about 0.05 mg/kg to about 20 mg/kg, and preferably from about 0.01 mg/kg to about 1 mg/kg.

EXAMPLES

Background for Examples 1 to 7

Metastasis is the primary cause of fatality in breast cancer patients. Although there are believed to be numerous events contributing to the process of metastasis, it is widely accepted that the loss of cell-to-cell adhesion in neoplastic epithelium is necessary for invasion of surrounding stromal elements and subsequent metastatic events. Cell-to-cell adhesion in epithelial cell sheets is maintained mainly through two types of junctions: adherens junctions and tight junctions.

Numerous studies have focused their attention on the transmembrane protein of the adherens junction, E-cadherin. These studies have shown that impairing the function of E-cadherin can cause cell dispersion and confer invasive properties in various cell types. Owing to these abilities, E-cadherin is believed to function as a tumor suppressor in numerous tissues and has been shown to be a useful prognostic indicator for some tumors, illustrating the importance of cell-to-cell adhesion proteins in cancer progression (Soler et al., 1995; Wheelock et al., 2001).

Tight junctions, unlike adherens junctions, are solely involved in cell-to-cell adhesion and serve two main functions in epithelial cell layers. First, they prevent the paracellular transport of solutes and ions, maintaining concentration gradients driving transcellular transport. Second, tight junctions prevent the diffusion of membrane proteins and lipids from the apical layer to the basolateral layer of an epithelial cell sheet, helping to maintain cell polarity (Mitic and Anderson, 1998).

Although tight junctions have clearly been shown to play a role in cell-to-cell adhesion, their potential role in cancer progression has been scarcely studied. This may be due, in part, to the lack of knowledge concerning the protein components of these junctions. However, in 1998, Tsukita et al. discovered a new family of tight junction proteins named Claudins (CLDNs) (Furuse et al., 1998). Currently, there are 20 known members of the CLDN family (Mitic et al., 2000). CLDNs contain four transmembrane domains and two extracellular loops through which they bind to CLDNs on adjacent cells (Morita et al., 1999). CLDNs have also been shown to bind to the tight junction protein ZO-1 through their carboxyl terminus (Itoh et al., 1999). Interestingly, ZO-1 is believed to interact with several proteins involved in cell signaling and transcriptional regulation (Balda and Matter, 2000; Mitic et al., 2000). These studies suggest that CLDNs may play an indirect role in cell signaling and transcriptional regulatory events. Most importantly, studies have shown CLDNs to be the main sealing proteins of the tight junction (Tsukita and Furuse, 1999).

Although changes in the permeability of tight junctions have been observed in several types of cancer, little is known about the role of CLDNs in cancer. In one such investigation, CLDN-1 cDNA levels were found to be decreased in a number of breast tumors and breast cancer cell lines (Kramer et al., 2000). Kramer et al. (2000) went on to examine the genetic status of CLDN-1 in a large number of sporadic and hereditary breast cancers, but found no genetic alterations that could explain this loss or provide evidence supporting the involvement of aberrant CLDN-1 in breast tumorigenesis.

Here we present, for the first time, data showing that expression of the tight junction protein CLDN-7 is lost in ductal carcinoma in situ (DCIS), lobular carcinoma in situ (LCIS), and invasive ductal carcinoma (IDC) of the breast relative to normal mammary epithelium. Loss of CLDN-7 closely associates with the discohesive architecture typically observed in high-grade lesions, suggesting a potential functional role for CLDN-7 in breast cancer progression. While the mechanism of loss of CLDN-7 in breast cancer cell lines could be ascribed to promoter hypermethylation (Jones and Baylin, 2002), this was not found to be the case in primary IDCs. Taken together, these studies suggest that the loss of CLDN-7 may aid the dissemination of cancer cells. Further, a second claudin, claudin-1, has been shown to exhibit similar properties.

Materials and Methods for Examples 1-7

Cell lines, Organoids and Tumors

Most cell lines were obtained from American Type Culture Collection (Manassas, Va., USA), and cultured according to conditions specified. Finite lifespan HMECs 9F1403, 04372, 16637 were purchased from Clonetics (Rockville, Md., USA). Breast cancer cell lines 21PT and 211MT; New England 184, immortalized HMECs 184A1 (early and late passages), 184B5; HMEC strain 11-24; were provided as gifts. Mammary organoid samples, N1, N34, N65, and N74 were prepared from reduction mammoplasty specimens of women with no abnormalities in the breast as described (Bergstraessar and Weitzman, 1993). Briefly, the specimens were enzymatically digested into duct-like structures (organoids), filtered, histologically confirmed to contain greater than 80% epithelial cells, and frozen at −70° C. until use (Bergstraessar and Weitzman, 1993). Highly purified (95-99%) luminal and myoepithelial cells were isolated by differential centrifugation and fluorescence-activated cell sorting of enzymatically digested normal mammoplasty specimens (Gomm et al., 1995). Paraffin blocks of DCIS, LCIS, and LDCs of the breast were obtained from the Surgical Pathology files of the Johns Hopkins Hospital, observing institutional guidelines for acquisition of such specimens.

Generation of CLDN-7 Antibody

A synthetic peptide corresponding to the C-terminus of CLDN-7 protein conjugated to the carrier protein, keyhole limpet hemocyanin (H) was generated by Mimotopes (Raleigh, N.C., USA). Polyclonal rabbit antipeptide antibodies were raised and sera were collected. CLDN-7 polyclonal antibody was then affinity purified using the Aminolink Immobilization kit (Pierce, Rockford, Ill., USA) and the peptide against which the antibody was raised. To test the affinity-purified CLDN-7 antibody for crossreactivity with other CLDN proteins, human CLDN-3-, -4, and -7 were cloned into pCR 3.1 (Invitrogen, Carlsbad, Calif., USA). CLDN-3, -4, and -7 proteins were generated in vitro using cDNA clones in the TnT Quick Coupled Transcription/Translation System (Promega, Madison, Wis., USA).

Immunofluorescence Microscopy

Cells ($1 \times 10^5$) were plated in eight-chamber slides (Nunc, Naperville, Ill., USA) and cultured until confluent. Cells were rinsed in phosphate-buffered saline (PBS) and fixed in 2% paraformaldehyde diluted in PBS for 15 min. Cells were then permeabilized in 0.5% Triton-X diluted in PBS for 5 min. Following permeabilization, cells were incubated in 20 mg/ml bovine serum albumin for 1 h at room temperature. Rabbit polyclonal CLDN-7 antibody diluted at 1:500 was then added to the cells and incubated at room temperature for 1 h. Subsequently, cells were incubated with mouse monoclonal 0-1 antibody (Zymed, San Francisco, Calif., USA) for 1 h at room temperature. Cells were then incubated with anti-rabbit IgG conjugated to Alexafluor 568 and anti-mouse IgG conjugated to Alexafluor 488 (Molecular Probes, Eugene, Oreg., USA) for 1 h at room temperature. Before visualizing the cells, sections were coverslipped and sealed.

Confocal Microscopy

Images were obtained using a Nikon PCM 2000.

Immunohistochemistry

Paraffin-embedded sections and breast tumor array sections were deparaffinized in xylene and rehydrated through graded ethanols. Antigen retrieval was performed by immersing sections in 0.01 m sodium citrate, pH 6.0, and boiling by microwave for 20 min. Sections were then cooled to room temperature and endogenous peroxidase activity was quenched by immersing in 0.3% hydrogen peroxide for 30 min. Blocking was then performed by incubation in diluted normal goat serum (Vectastain kit, Vector, Burlingame, Mich., USA) as per the manufacturer's instructions. Sections were then incubated with rabbit polyclonal CLDN-7 at a 1:500 dilution for a period of 16 h. Diluted biotinylated anti-rabbit IgG (Vectastain kit) was added to the sections and incubated for 30 min. Vectastain ABC reagent was then added for 30 min. CLDN-7 protein was visualized using 3,30-diaminobenzamidine (DAB) as per the manufacturer's instructions (Vector). Sections were then counterstained in hematoxylin (Richard-Allan Scientific, Kalamazoo, Mich., USA) for 10 s. Lastly, sections were dehydrated through graded ethanols, cleared in xylene, mounted, and coverslipped. Images were acquired by light microscopy.

Statistical Analysis of CLDN-7 Expression

IHC staining of CLDN-7 in DCIS, LCIS, and IDC lesions was scored relative to adjacent normal mammary epithelium as positive (no change in expression) or negative (loss of expression). Comparisons of CLDN-7 expression across grade were made by tabulating scores for CLDN-7 staining according to histological grade (Nuclear or Elston grades 1, 2, or 3). Two-sided Fisher's exact tests were used to assess statistical significance. Although grade is an ordinal variable, the analysis treated it as nominal categorical. As such, P values are slightly conservative. Inverse correlation implies that as histological grade tends to higher values, CLDN-7 is less likely to be expressed.

Methylation-Specific PCR

Genomic DNA (1 µg) was treated with sodium bisulfite as previously described (Ferguson et al., 2000) and was analysed by MSP using primer sets located within a CpG-rich area in the CLDN-7 promoter (GenBank Accession #11425795) Primers specific for unmethylated DNA were 5'-TGGG-GAAAGGGTGGTGTTG-3' (SEQ ID NO: 2) (sense, -831 to -812) and 5'-TTACCCAATTTTAACCACCAC-3' (SEQ ID NO: 3) (antisense, -670 to -649) yielding a 182 bp product. Primers specific for methylated DNA were 5'-GACGTTAG-GTTATTTTCGGTC-3' (SEQ ID NO: 4) (sense, -550 to -529) and 5'-AAACGCGTTTCTAAACGCCG-3' (SEQ ID NO: 5) (antisense, -350 to -330) yielding a 220 bp product. The PCR conditions were as follows: one cycle of 95° C. for 5 min 'hot start,' then addition of 1 ml Taq polymerase (Red-Taq, Sigma, St Louis, Mo., USA); 35 cycles of 95° C. for 30 s, 56° C. for 30 s, and 72° C. for 45 s; and one cycle of 72° C. for 5 min. PCR samples were resolved by electrophoresis on a 1.5% agarose gel.

5-aza-dC Treatment

Cells were seeded in a 100 mm plate at a density of 1×10$^6$ cells. After 24 h, cells were treated with 0.75 mm 5-aza-dC (Sigma) (Ferguson et al., 2000; Evron et al., 2001a, b). Total to cellular DNA and RNA were isolated at 0, 3, and 5 days after addition of 5-aza-dC.

RT-PCR.

Total RNA was extracted using TRI REAGENT BD by the manufacturer's protocol (Molecular Research Center, Cincinnati, Ohio, USA). cDNA was generated by reverse transcription. Reactions contained 2 mg DNAse-treated RNA, 0.25 mg/µl pdN6 random primers (Life Technologies, Rockville, Md., USA), 1× first-strand buffer (Life Technologies), 1 mm of each deoxynucleotide triphosphate (Life Technologies), 200 units Superscript reverse transcriptase (Life Technologies), and were incubated for 1 h at 37° C., followed by heat inactivation at 70° C. for 15 min. PCR was performed using the primers 5'-CCACTCGAGCCCTAATGGTG-3' (SEQ ID NO: 6) (sense) and 5'-GGTACCCAGCCT-TGCTCTCA-3' (SEQ ID NO: 7) (anti-sense) for CLDN-7 (Accession #AJ011497). Coamplified products of 36B4, a 'housekeeping' ribosomal protein gene, were used as an internal control, using primers 5'-GATTGGCTACCCAACTGT-TGCA-3' (SEQ ID NO: 8) and 5'-CAGGGGCAGCAGCCA-CAAAGGC-3' (SEQ ID NO: 9) for sense and antisense, respectively. The 25 ml reactions contained 1× buffer (2× reaction mix, Life Technologies), 1 µl cDNA, and 10 nm of each primer. The PCR conditions were: one cycle of 94° C. for 1 min, 'hot start,' followed by addition of one unit of Taq polymerase (RedTaq, Sigma), 35 cycles of 94° C. for 30 s, 59° C. for 30 s, 72° C. for 45 s, and finally one cycle of 72° C. for 5 min. PCR samples were resolved by electrophoresis on a 1.5% agarose gel.

Real-Time PCR

Total RNA was extracted and cDNA was generated by reverse transcription as described above. CLDN-7 and GAPDH (a 'housekeeping' gene) were amplified individually using a 96-well plate and optical caps (PE Applied Biosystems, Foster City, Calif., USA) with a 25 µl final reaction volume containing 250 nmol/l sense and antisense primer, 200 nmol/l probe, 2.5 mm MgCl$_2$, one unit Amplitaq Gold, 200 mmol/l each of dATP, dCTP, dTTP, and dGTP in 1× Taqman Buffer A. Reaction mixtures were preheated to 95° C. for 10 min, followed by 40 cycles at 95° C. for 15 s and 60° C. for 1 min. The primer and probe sequences are as follows: CLDN-7 (sense) 5'-AAAG TGAAGAAGGCCCGTATAGC-3'(SEQ ID NO: 10), CLDN-7 (antisense) 5'-GCTACCAAG-GCGGCAAGAC-3' (SEQ ID NO: 11), CLDN-7 (probe) 5'-CC ACGATGAAATTATGCCTCCACCCA-3'(SEQ ID NO: 12), GAPDH (sense) 5'-CCCATGTTCGT-CATGGGTGT-3' (SEQ ID NO: 13), GAPDH (antisense) 5'-TGGTCATGAGTCCTTCCACGATA-3' (SEQ ID NO: 14), and GAPDH (probe) 5'-CTGCACCACCAACTGCT-TAG-3' (SEQ ID NO: 15). All PCR reagents, including primers and probes, were purchased from PE Applied Biosystems.

Sequencing of Sodium-bisulfite-Treated DNA

DNA from peripheral white blood cells, IDCs, and breast cancer cell lines was treated with sodium bisulfite as previously described (Ferguson et al., 2000). Briefly, the DNA was purified and a CpG-rich promoter region was amplified by PCR using the following primers: 5'-GTGATTTTGGTGTT-TAGGT-3' (SEQ ID NO: 16) (sense primer with start at -675) and 5'-ATCCCAAAATATCCTAAACTA-3' (SEQ ID NO: 17) (antisense primer with start at -375), which generated a 300 bp PCR product. The product was purified using a Qiagen PCR purification kit (Qiagen Corp) and sequenced using the antisense primer.

Western Blotting

IDC of the breast and normal mammary organoid tissue was homogenized and total protein was extracted using lysis buffer consisting of 15% glycerol, 5% SDS, and 250 mm Tris-HCl, pH 6.7. Equal amounts of protein from cell lysates were resolved using 12% SDS-PAGE (Invitrogen, Carlsbad, Calif., USA). Protein was then transferred to ECL nitrocellulose membranes (Amersham, Arlington Heights, Ill., USA). Following Western transfer, membranes were probed with CLDN-3, 4(Zymed), CLDN-7, or b-actin (Amersham) antibody diluted 1:1000 (CLDN-3, 4, and 7) or 1:5000 (bactin). Horseradish peroxidase-conjugated antibody against rabbit or mouse IgG (Amersham) was used at 1:1000 and binding was revealed using enhanced chemiluminescence (Amersham).

Abbreviations

CLDN, Claudin; IDC, invasive ductal carcinoma; RT-PCR, reverse transcription—polymerization chain reaction; IHC, immunohistochemical analysis; DCIS, ductal carcinoma in situ; LCIS, lobular carcinoma in situ; HGF/scatter factor, hepatocyte growth factor/scatter factor; KLH, keyhole limpet hemocyanin; MSP, methylation-specific PCR; DAB, 3 3'-diaminobenzamidine; GAPDH, glyceraldehyde phosphate dehydrogenase; 5-aza-dC, 5'-aza-2'-deoxycytidine; HMEC, human mammary epithelial cells.

Example 1

Expression of CLDN-7 mRNA in IDC and Normal Mammary Epithelium

A SAGE and cDNA microarray analysis performed previously in our laboratory had suggested that CLDN-7 was overexpressed in breast cancer cell lines and IDCs of the breast relative to cultured finite lifespan human mammary epithelial cells (HMEC) (Nacht et al., 1999). We initiated validation studies by directly comparing the expression of a number of differentially expressed mRNAs in IDCs using semiquantitative RT-PCR analysis. Total RNA was extracted and cDNA was generated by reverse transcription. CLDN-7 and 36B4, a 'housekeeping' ribosomal protein gene, were amplified individually by PCR. PCR products were resolved by electrophoresis on a 1.5% agarose gel. Samples were: 16637- and 04372-cultured HMECs from Clonetics; Lum 1-4 and Myo 1-3-Immunobead purified luminal and myoepithelial cells from normal mammoplasty specimens; and 10 invasive ductal carcinomas. Confirming data from microarray analysis (Nacht et al., 1999), CLDN-7 expression was undetectable by RT-PCR in finite lifespan HMECs expanded in tissue culture, 16637 and 04372, and in HMEC 184, 184A1 (early and late passage) and 184B1 (data not shown). Contrary to our expectation, however, easily detectable to high levels of CLDN-7 mRNA expression were seen in seven of seven uncultured luminal and myoepithelial cell populations derived from normal mammoplasty specimens. Also, nine of ten IDCs showed low or undetectable levels of CLDN-7 mRNA. These observations were in direct contrast to our published data (Nacht et al., 1999), where we had reported that at least 50% of primary tumors express levels of CLDN-7 mRNA that were significantly higher than cultured finite lifespan HMEC.

Figure 1:
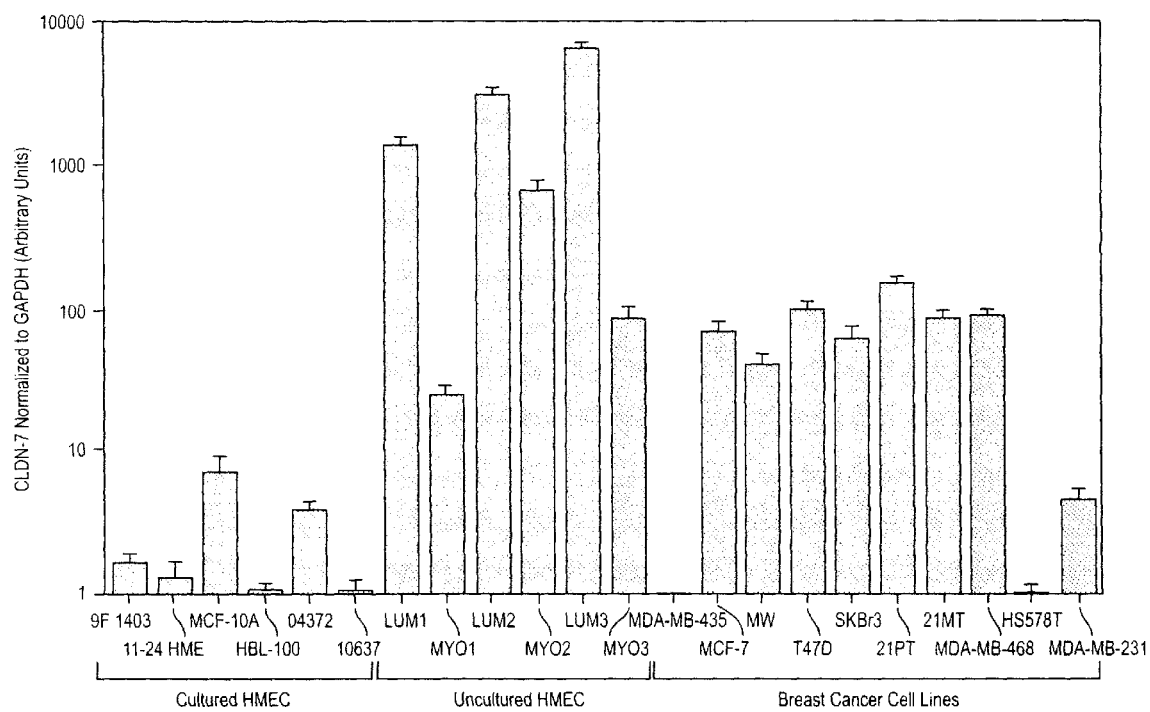
FIG. 1: CLDN-7 mRNA expression in invasive ductal carcinomas, uncultured luminal (Lum) and myoepithelial (Myo) human mammary epithelial cells (uncultured HMEC), and human mammary epithelial cells cultured in vitro (cultured HMEC). Total RNA was extracted and cDNA was generated by reverse transcription. CLDN-7 and GAPDH (a "housekeeping" gene) were amplified individually by real-time PCR. CLDN-7 expression levels were normalized to levels of GAPDH, multiplied by $(10)^3$, and reported in arbitrary units +/−s.d. Data are from experiments performed in triplicate.

One possible explanation for these contradictory findings could be the choice of HMEC used to compare expression profiles between normal and tumor samples. In our study, as in many other comparative gene expression profiling studies (Fujii et al., 2002; Iacobuzio-Donahue et al., 2002), we had used mortal HMEC expanded in tissue culture as our source of normal breast epithelium. We considered the possibility that placing the cells in tissue culture, albeit short term, may have altered their expression profile and resulted in a loss of CLDN-7 expression. To test this possibility, we determined the expression of CLDN-7 in two immortalized and four finite lifespan HMEC cultured in vitro, six uncultured HMEC derived from three normal mammoplasty specimens, and 10 breast cancer cell lines by realtime PCR analysis (FIG. 1). A striking difference in CLDN-7 mRNA expression was observed between the six tissue cultured cell lines (n=2) and strains (n=4) and the six uncultured HMEC. HMEC cultured in vitro showed very low to undetectable levels of CLDN-7 mRNA expression, while an average of nearly 1000-fold higher levels were observed in uncultured HMEC, of both luminal and myoepithelial subfractions. Thus, the erroneous conclusion of CLDN-7 overexpression in primary tumors likely arose as a consequence of using cultured HMEC (which expressed extremely low levels of CLDN-7 mRNA) as a basis for comparison. Relative to CLDN-7 mRNA levels in uncultured HMEC, however, CLDN-7 expression in all breast cancer cell lines was lower by 10-1000-fold. Thus, although immaterial for many other genes (Ferguson et al., 2000; Evron et al., 2001a, b; Loeb et al., 2001), placing HMEC in tissue culture had the profound effect of silencing CLDN-7 expression. When used as controls for comparative gene expression studies, such tissue-culture-based alterations could lead to inaccurate interpretation of data.

This example demonstrates that CLDN-7 is consistently expressed in normal mammary epithelium which CLDN-7 expression is lost in approximately 70% of primary breast carcinomas.

Example 2

Generation and Characterization of CLDN-7 Polyclonal Antibody

Figure 2:
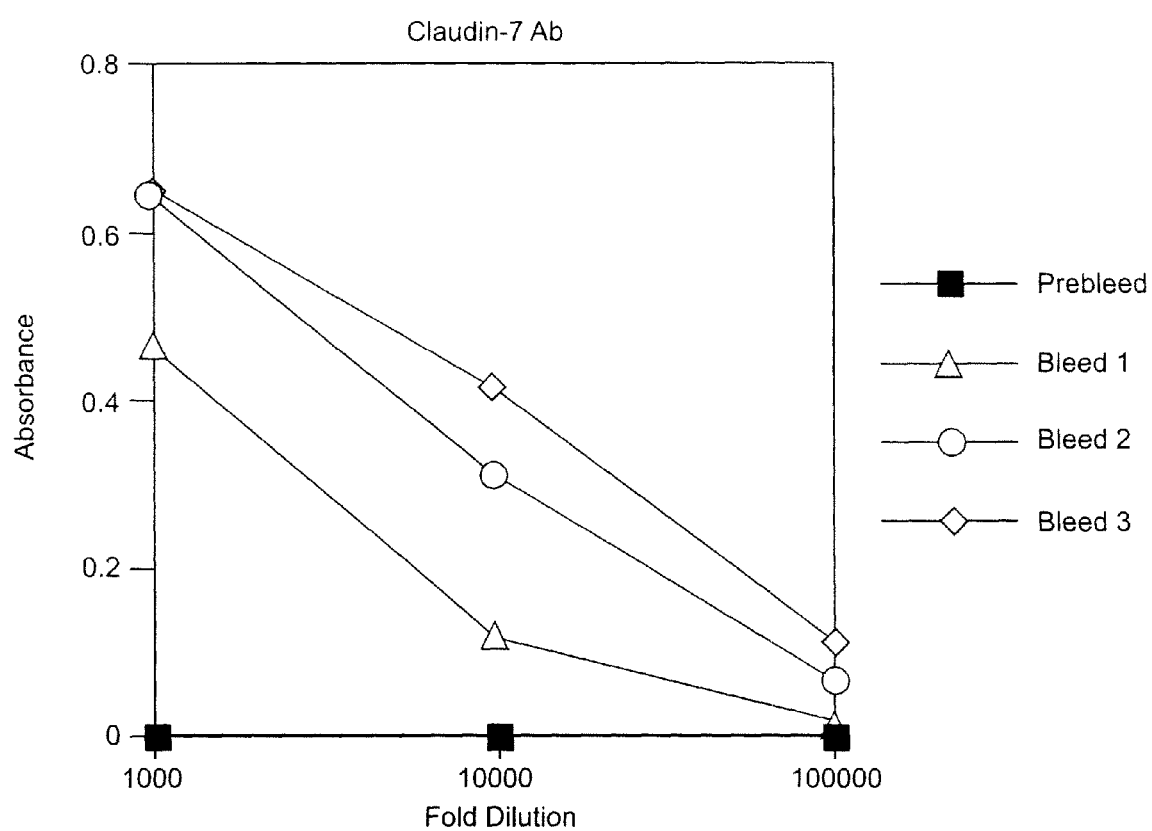
FIG. 2: Claudin-7 polyclonal antibody production and detection by ELISA.

To study expression of CLDN-7 protein in breast tissues, we generated a rabbit polyclonal antibody against the synthetic polypeptide CKAGYRAPRSYPKSNSSKEYV (SEQ ID NO: 1) corresponding to the C-terminus of CLDN-7. This region of the protein shares little sequence similarity with other members of the CLDN family. Human CLDN-3, -4, and -7 were cloned into pCR 3.1 (Invitrogen) and proteins were generated in vitro using cDNA clones in the TnT Quick Coupled Transcription/Translation System as determined by Western analysis using antibodies specific for CLDN-3 and -4 (Zymed). Next, we used the C-terminal CLDN-7 peptide in enzyme-linked immunosorbent assay (ELISA) to test for the presence of CLDN-7 antibody in rabbit sera. The results are shown in FIG. 2 where CLDN-7 antibody is detected in rabbit sera from bleeds 1-3 as indicated by a linearly increased level of absorbance over several folds dilution versus no absorbance detected in rabbit sera from prebleed (blood drawn prior to antigen delivery). The CLDN-7 antibody was affinity purified using the peptide against which it was raised. Western analysis was performed on equal amounts of protein from TnT reactions using CLDN-7 antibody producing a single band at the predicted size of approximately 23 kDa, while not detecting CLDN-3 or -4. Conversely, antibodies to CLDN-3 and -4 did not detect CLDN-7 protein, but detected their cognate protein. Further, preincubation of CLDN-7 antibody with the C-terminal peptide was able to compete out binding to CLDN-7 protein in Western analysis (data not shown).

To perform immunofluorescence studies using the affinity purified antibody, MCF-7 cells were grown to confluence on a chambered slide, and probed with CLDN-7 and ZO-1 antibodies. CLDN-7 and ZO-1 proteins were visualized both individually and as a composite by confocal microscopy at a magnification of ×600. The results showed colocalization of CLDN-7 with the tight junction protein ZO-1 at the cell membrane. Unique red spots were observed in the cytoplasm. Whether they represent nonspecific staining or CLDN-7 localized in cell organlles is not yet known. These spots were not localized to mitochondria, however, since they did not colocalize with organelles stained by using the MitoTracker Red dye (Molecular Probes, Eugene Oreg.).

This example demonstrates that affinity purified CLDN-7 antibody recognizes CLDN-7 at the cell membrane and more specifically at the tight junction.

Example 3

Expression of CLDN-7 Protein in IDC and Normal Mammary Epithelium

To determine whether protein expression reflected that of CLDN-7 mRNA expression as obtained by RT-PCR, we performed Western analysis on a panel of 10 breast cancer cell lines, eight IDCs, and four samples of mammary organoids isolated from reduction mammoplasty specimens of normal women. Western analysis was performed on equal amounts of protein from total cell lysates using CLDN-7 and b-actin antibodies. Consistent with real-time quantitative RT-PCR results (FIG. 1), Western analysis of a panel of 10 breast cancer cell lines showed a close correlation between CLDN-7 protein and CLDN-7 mRNA expression. Cell lines that showed low or no detectable mRNA (MDA-MB-435, MDA-MB-231, and HS578T) had no detectable protein, while the remaining seven cell lines showed detectable CLDN-7 expression. Also consistent with RT-PCR, CLDN-7 expression in six of eight IDCs was significantly lower than in four samples of epithelial organoids obtained by enzymatic digestion of normal mammoplasty specimens. Lastly, Claudin-1 expression was found to be down-regulated in 6 out of 10 breast cancer cell lines as compared to immortalized and finite life-span normal human mammary epithelial cells. This is consistent with reports of frequent done-regulation of Claudin-1 in primary breast carcinoma.

Owing to the heterogeneity of cell types in breast tissue and the fact that only the epithelial cell component expresses CLDNs, it was necessary to determine if the loss of CLDN-7 expression observed in breast cancer tissues relative to normal mammary epithelium was simply because of a difference in epithelial cell content. Therefore, we performed immunohistochemical (IHC) analysis on several of the same IDC cases that had been tested by Western analysis. IDC analysis was performed on paraffin-embedded sections of human breast cancer tissues 079, 126, and 973 using CLDN-7 antibody. CLDN-7 protein in human breast cancer tissues (T) and adjacent normal mammary epithelium (N) were visualized using DAB. Membrane staining was observed in normal breast epithelium. Sections were counterstained with hematoxylin and visualized by light microscopy (×200) In each case, the CLDN-7 staining pattern was compared to that in adjacent normal epithelium as an internal positive control. Surrounding fibroblasts and adipocytes served as negative controls since these cells do not express CLDN proteins. The analysis was performed on equal amounts of protein from cell lysates using CLDN-7 and b-actin antibodies.

As expected for a tight junction protein, CLDN-7 staining was restricted to epithelial cells with the strongest expression concentrated at the cell membrane, although diffuse staining in the cytoplasm was also observed. Consistent with the Western analysis results, the level of CLDN-7 staining was greatly reduced in all three IDCs tested as compared to adjacent normal epithelium.

This example demonstrates that CLDN-7 protein expression is lost in primary breast carcinoma cells relative to normal mammary epithelium.

Example 4

Expression of CLDN-7 in Ductal Carcinoma In Situ and IDC

To assess the potential value of loss of CLDN-7 as a prognostic indicator for breast cancer, we determined its expression pattern in a series of in situ and invasive breast carcinomas by IHC analysis. As DCIS is believed to be a direct precursor to IDC, we first examined the CLDN-7 staining pattern in a range of DCIS cases, from nuclear grade 1 (low grade) through 3 (high grade). In each case, the staining pattern of CLDN-7 in DCIS was compared to that in adjacent normal epithelium, where staining was predominantly membranous. IHC analysis showed no changes in CLDN-7 expression in either grade 1 (0/10) or grade 2 (0/14) cases, while 71% of grade 3 cases (10/14) showed a loss of its expression (Table 1). Thus, we observed that CLDN-7 expression in DCIS was inversely correlated with nuclear grade (P<0.001).

We next examined the CLDN-7 staining pattern in IDCs ranging from Elston grade 1 (low grade) through 3 (high grade), which was compared in each case to that seen in the normal epithelium present on the same section. IHC analysis was performed on paraffin-embedded sections of human breast tissue using CLDN-7 antibody. CLDN-7 protein was visualized using DAB. Sections were counterstained in hematoxylin and visualized by light microscopy (×200). Membrane staining of normal breast epithelium was noted. Few grade 1 (1/6) or grade 2 (3/12) IDC cases showed a loss of CLDN-7 expression, while 77% of grade 3 cases (10/3) showed a significant loss of staining (Table 1). Thus, CLDN-7 expression in IDC was found to be inversely correlated with histological grade (P=0.014).

CLDN-7 immunoreactivity in IDC was further studied by tissue array analysis. IDC analysis was performed on tissue arrays containing 612 paraffin-embedded sections of human breast tissue using CLDN-7 antibody. CLDN-7 protein was visualized using DAB. Sections were counterstained in hematoxylin and visualized by light microscopy (×200) Of the 612 total cases of IDC on the tissue array, 100 Elston grade 1, 140 Elston grade 2, and 115 Elston grade 3 cases were evaluable and showed an inverse correlation between CLDN-7 expression and histological grade (P=0.03). This finding was consistent with the results of the case-by-case analysis (summarized in Table 1).

TABLE 1

IHC analysis of CLDN-7 expression[a]

| Histology | Histological grade | Cases with loss of expression/total cases | P[b] |
|---|---|---|---|
| DCIS | Nuclear grade | | |
| | 1 | 0/10 | |
| | 2 | 0/14 | |
| | 3 | 10/14 | <0.001 |
| IDC | Elston Grade | | |
| | 1 | 1/6 | |
| | 2 | 3/12 | |
| | 3 | 10/13 | 0.014 |
| LCIS | NA | 13/17 | |

[a]Data are compiled from IHC analysis of whole paraffin-embedded sections
[b]Comparisons of CLDN-7 expression across grade were made by tabulating scores for CLDN-7 staining according to histological grade (nuclear or Elston grades 1, 2, or 3) Two-sided Fisher's exact tests were used to assess statistical significance No correlation between CLDN-7 expression and estrogen/progesterone receptor status, age, tumor size, or lymph node status was found by tissue array analysis. This last result was contrary to our case-by-case analysis, where seven of ten IDCs with a positive lymph node status showed a loss of CLDN-7 expression. While the utility of tissue arrays cannot be underestimated since it allows for very high sample throughput, the lack of an internal control (normal epithelium) for each tumor sample, combined with the small sampling represented in each tissue punch could lead to a greater error in determining gene expression. In our study, these factors may be responsible for the lack of correlation with lymph node status in tissue arrays when compared to case-by-case analysis. This source of error is being minimized in newer generations of tissue arrays, which contain several punches from the same tumor tissue, and also from their normal margins. Thus, at the present time, performing a case-by-case analysis alongside tissue array analysis is preferred.

This example demonstrates that expression of CLDN-7 is inversely correlated with tumor grade, being lost in the majority of high grade DCIS and high grade IDC lesions, suggesting that CLDN-7 will be useful as a prognostic marker for breast cancer.

Example 5

Expression of CLDN-7 in LCIs

If CLDNs play a functional role in cell-to-cell adhesion, breast lesions that are typified by scattered cells should express very low levels of CLDN-7. In agreement with this notion, IHC analysis of LCIS, a lesion whose defining and characteristic feature is discohesion, was carried out. IHC analysis was performed on paraffin-embedded sections of human breast tissue using CLDN-7 antibody. CLDN-7 protein was visualized using DAB. Sections were counterstained in hematoxylin and visualized by light microscopy (×200). The results showed a loss of CLDN-7 expression in 76% (13/17) of cases. This contrasted significantly (P=0.001) with DCIS, where its loss is seen in only 26% (10/38) of cases irrespective of grade (Table 1).

This example demonstrates that loss of CLDN-7 expression correlates with cellular discohesiveness.

Example 6

Effect of HGF/Scatter Factor on CLDN-7 Expression

A direct demonstration of the inverse correlation between CLDN-7 expression and cell-to-cell adhesion was sought by the treatment of breast cancer cell lines with hepatocyte growth factor/scatter factor (HGF/scatter factor). HGF is well known for its ability to decrease cell-to-cell adhesion and stimulate cell migration (Jiang et al., 1999). Breast cancer cell lines MCF-7 and T47D, which express high levels of CLDN-7 localized at the tight junction were treated with HGF/scatter factor for a period of 24 h. Western analysis was performed on equal amounts of total cell lysate using CLDN-7 and b-actin antibodies. The results showed a dramatic downregulation of CLDN-7 was observed in MCF-7, and to a lesser extent in T47D cells.

These data provide further direct evidence that loss of CLDN-7 occurs concurrently with loss of cell-to-cell adhesion.

Example 7

Mechanism of Loss of CLDN-7 Expression in Breast Cancer

To investigate the mechanism responsible for the loss of CLDN-7 expression, we first wanted to rule out the presence of mutations in the CLDN-7 mRNA (Accession #AJ011497) sequence. Nucleotide sequencing of the full-length cDNA revealed no mutations in the CLDN-7 coding sequences in all 11 primary LDCs tested (data not shown). Among the 11 tumors, six expressed very low or no CLDN-7 mRNA as determined by semiquantitative RT-PCR analysis.

The presence of CG-dinucleotide-rich sequences in the promoter region of genes is quite often a signature denoting that hypermethylation may be a potential mechanism for gene silencing (Ferguson et al., 2000; Evron et al., 2001a, b; Loeb et al., 2001; Jones and Baylin, 2002). The CLDN-7 promoter contains a CpG-rich region extending from −20 to −900 bp upstream of the translational start site (Accession #11425795). Therefore, we investigated the promoter region of the CLDN-7 gene. Methylation-specific PCR (MSP) analysis was performed on DNA from six breast cancer cell lines. Methylated (M) and unmethylated (UM) gene sequences were amplified individually by MSP using sodium-bisulfite-treated DNA from breast cancer cell lines. WBC (peripheral blood cells) served as a negative control. MSP products were resolved by electrophoresis on a 1.5% agarose gel. The three breast cancer cell lines that show no detectable CLDN-7 expression (HS578T, MDA-MB-231, and MDA-MB-435) contained hypermethylated promoter sequences, while the three that express CLDN-7 (T47D, MCF-7, and MNDA-MB-468) were unmethylated in the same region.

This correlation between the loss of CLDN-7 expression and promoter hypermethylation was further confirmed by sequencing a 300 bp region (containing a dense region of 25 CpG dinucleotides, and included the CG-rich region analysed by MSP) of the CLDN-7 promoter, PCR-amplified from sodium-bisulfite-treated DNA. All 25 CpGs were methylated in HS578T, MDA-MB-231, and MDA-MB-435 cells, while MCF-7 cells contained no methylated CpGs (data not shown).

Lastly, treatment of HS57ST and MDA-MB-435 cells with the demethylating agent, 5-aza-dC, resulted in the re-expression of CLDN-7. RT-PCR was performed for CLDN-7 and -36B4, a 'housekeeping' ribosomal protein gene. PCR products were resolved by electrophoresis on a 1.5% agarose gel. The results clearly showed that hypermethylation is a major mechanism responsible for silencing expression of CLDN-7 in breast cancer cell lines, and provides another line of evidence supporting the premise that hypermethylation is a major mechanism responsible for silencing expression of CLDN-7 in breast cancer cell lines.

Next, to determine if hypermethylation-mediated silencing of CLDN-7 expression is functional in primary breast cancer as well, we performed MSP analysis on DNA from IDCs. As expected, the sample of normal mammary organoid, N65, and two IDC samples that express CLDN-7 were unmethylated in this region. However, contrary to our findings in breast cancer cell lines, MSP analysis of the CLDN-7 promoter in the five IDCs that have lost CLDN-7 expression also showed completely unmethylated promoter sequences. Since MSP analyses only a few CpGs in the promoter, we sequenced the 300 bp segment of the promoter described above. Sequencing of sodium-bisulfite-treated DNA from IDCs 079 and 973 showed no methylated CpGs (data not shown).

Thus, the evidence provided by MSP, nucleotide sequencing analysis, and re-expression of genes following 5-aza-dC treatment, strongly support the notion that promoter hypermethylation of CLDN-7 is the underlying mechanism for loss of its expression in breast cancer cell lines.

References for Examples 1-7

Balda M S and Matter K. (2000). EMBO J., 19, 2024-2033.
Bergstraessar L M and Weitzman S A. (1993). Cancer Res., 53, 2644-2654.
Evron E, Dooley W C, Umbricht C B, Rosenthal D, Sacchi N, Gabrielson E, Soito A B, Hung D T, Ljung B, Davidson N E and Sukumar S. (2001a). Lancet, 357, 1335-1336.
Evron E, Umbricht C B, Korz D, Raman V, Loeb D M, Niranjan B, Buluwela L, Weitzman S A, Marks J and Sukumar S. (2001b). Cancer Res., 61, 2782-2787.
Ferguson A T, Evron E, Umbricht C B, Pandita T K, Chan T A, Herneking H, Marks J R, Lambers A R, Futreal P A, Stampfer M R and Sukumar S. (2000). Proc. Natl. Acad. Sci. USA, 97, 6049-6054.
Fujii T, Dracheva T, Player A, Chacko S, Clifford R, Strausberg R L, Buetow K, Azumi N, Travis W D and Jen J. (2002). Cancer Res., 62, 3340-3346.
Furuse M, Fujita K, Hiiragi T, Fujimoto K and Tsukita S. (1998). J. Cell Biol., 141, 1539-1550.
Furuse M, Hata M, Furuse K, Yoshida Y, Haratake A, Sugitani Y, Noda T, Kubo A and Tsukita S. (2002). J. Cell Biol., 156, 1099-1111.
Gomm J J, Browne P J, Coope R C, Liu Q Y, Buluwela L and Coombes R C. (1995). Anal. Biochem., 226, 91-99.
Iacobuzio-Donahue C A, Maitra A, Shen-Ong G L, van Heek T, Ashfaq R, Meyer R, Walter K, Berg K, Hollingsworth M A, Cameron J L, Yeo C J, Kern S E, Goggins M and Hruban R H. (2002). Am. J. Pathol., 160, 1239-1249.
Itoh M, Furuse M, Morita K, Kubota K, Saitoti M and Tsukita S. (1999). J. Cell Biol., 147, 1351-1363.
Jiang W, Hiscox S, Matsumoto K and Nakamura T. (1999). Crit. Rev. Oncology Hematology, 29, 209-248.
Jones P A and Baylin S B. (2002). Nat Rev Genet., 3, 415-428.

Kramer F, White K, Kubbies M, Swisshelm K and Weber B H F. (2000). Hum. Genet., 107, 249-256.

Loeb D M, Evron E, Patel C B, Sharma P M, Niranjan B, Buluwela L, Weitzman S A, Korz D and Sukumar S. (2001). Cancer Res., 61, 921-925.

Mitic L L and Anderson J M. (1998). Annu. Rev. Physiol., 60, 121-142.

Mitic L L, Van Itallie C M and Anderson J M. (2000). Am. J. Physiol. Gastrointest. Liver Physiol., 279, G250-G254.

Morita K, Furuse M, Fujimoto K and Tsukita S. (1999). Proc. Natl. Acad. Sci. USA, 96, 511-516.

Nacht M, Ferguson A T, Zhang W, Petroziello J M, Cook B P, Gao Y H, Maguire S, Riley D, Coppola G, Landes G M, Madden S L and Sukumar S. (1999). Cancer Res., 59, 5464-5470.

Simon D B, Lu Y, Choate K A, Velazques H, Al-Sabban E, Praga M, Casari C G Bettinelli A, Colussi G, Rodriguez-Soriano J et al. (1999). Science, 285, 103-106.

Sirotkin H, Morrow B, Saint-Jore B, Puech A, Das Gupta R, Patanjali S R, Skoultchi A, Weissman S M and Kucherlapati R. (1997). Genomics, 42, 245-251.

Soler A P, Knudsen K A, Jaurand M-C, Johnson K R, Wheelock M J, Klein-Szanto A J P and Salazar H. (1995). Hum. Pathol., 26, 1363-1369.

Tsukita S and Furuse M. (1999). Trends Cell Biol., 9, 268-273.

Wheelock M J, Soler A P and Knudsen K A. (2001). J. Mammary Gland Biol. Neoplasia, 6, 275-285.

Wilcox E R, Burton Q L, Naz S, Riazuddin S, Smith T N, Ploplis B, Belyantseva I, Ben-Yosef T, Liburd N A, Morell R J, Kachar B, Wu D K, Grifth A J, Riazuddin S and Friedman T B. (2001). Cell, 104, 165-172.

Background for Examples 8 to 15

Breast cancer therapies have shown limited efficacy in patients with advanced disease. Although many advances in diagnostic, prognostic, and therapeutic methods have been made over the last several years, breast cancer remains the second leading cause of cancer death in women and the leading cause of death in women between the ages of 40 and 55. Thus preventative and new therapeutic techniques are needed.

*Clostridium perfringens* enterotoxin (CPE) is a common cause of food poisoning. Following ingestion of CPE, the toxin binds to its receptors on intestinal epithelial cells resulting in cell lysis. The receptors for CPE were identified in 1999 as the tight junction proteins Claudin 3 and 4. Claudin 3 functions as the low affinity receptor and Claudin 4 as the high affinity receptor. We propose that CPE targeting through claudins 3 and 4 may provide an effective preventative measure as well as therapy for breast cancer. Further, patients afflicted with breast as well as lung, colon, kidney, and skin cancer frequently die from neurological complications resulting from metastases to the brain or bone. Several other varieties of carcinoma have been known to metastasize to the brain and bone as well including those of prostate and pancreas. Targeting claudins 3 and 4 with CPE may provide a means of eliminating these metastases from the brain and bone without damaging healthy tissues as normal brain and tissue does not express these proteins.

Materials and Methods for Examples 8-15

Reagents

Purified *Clostridium perfringens* enterotoxin was obtained as a gift. Antibodies against Claudin 3 and 4 were obtained from Zymed Laboratories.

Cell Lines

HBL-100 cells were maintained in growth medium consisting of McCoy's 5A medium supplemented with 10% fetal bovine serum (FBS). SKBr3 cells were maintained in growth medium consisting of McCoy's 5A medium supplemented with 15% fetal bovine serum (FBS). HS578T, MCF-7, MDA-MB 435, and NIH 3T3 cells were maintained in growth medium consisting of Dulbeccos modified eagles medium (DMEM) supplemented with 10% fetal bovine serum (FBS). T47D and MDA-MB 231 cells were maintained in growth medium consisting of RPMI medium supplemented with 10% fetal bovine serum (FBS). 21MT and 21 PT cells were maintained in growth medium consisting of alpha minimal essential medium supplemented with 10% fetal bovine serum (FBS), 10 mM HEPES, 1× non-essential amino acids, 1 mM sodium pyruvate, 2 mM glutamine, 1 μg/ml insulin, 25 ng/ml EGF, and 1 μg/ml hydrocortisol. MW cells were maintained in growth medium consisting of 45% DM-EM and 45% Ham's F 12 supplemented with 10% fetal bovine serum (FBS). MCF-10A cells were maintained in growth medium consisting of 47.5% DMEM and 47.5% Ham's F12 supplemented with 5% horse serum, 100 ng/ml cholera toxin, 10 μg/ml insulin, 0.5 μg/ml hydrocortisol, and 20 ng/ml EGF. NMU 36 and NMU 58 cells were maintained in growth medium consisting of 45% DMEM and 45% Ham's F 12 supplemented with 10% fetal bovine serum (FBS).

CPE Cytotoxicity

Cells were plated at $3\times10^5$ cells/well in 6-well plates and grown to 80% confluence. Media was then removed and replaced with fresh media with or without CPE at concentration ranging from 0.05 to 2 μg/ml. Cells were incubated at 37° C. for 60 min. Floating and attached cells were collected and counted using a hemocytometer. Cell viability was determined by trypan blue (0.4%) dye exclusion.

Detection of Claudin-3 and 4 in Blood and Ductal Lavage Fluid

Blood and ductal lavage fluid is collected from breast cancer patients. Red blood cells are then removed from whole blood by lysis in $H_2O$. Protein is then extracted from the remaining mixture of leukocytes ind cancer cells or ductal lavage fluid. Equal amounts of protein are then absorbed to a 96-well plate over night. Plates are then dried and incubated at room temperature (RT) in blocking buffer (50 g Milk/L PBS) for 2 hrs. Claudin-3 or 4 antibody (Zymed) is added to the plate and incubated for 2 hours at RT. Claudin-3 or 4 is detected following the addition of HRP substrate using a plate reader at 490 nm. HRP-labeled secondary antibody is then added and incubated for 1 hour. The presence of Claudin-3 or 4 is detected following the addition of HRP substrate using a plate reader at 490 mm.

Mouse Toxicity Studies 6-8 week old athymic nude and Balb/C mice were be anesthetized and a 2 mm burr hole centered 2 mm posterior to the coronal suture and 2 mm lateral to the sagittal suture was made. Mice were transferred to a stereotactic frame and administered either PBS or CPE (0.05-10 ug) as a single injection into the cerebral cortex at a depth of 3 mm three times per week for two weeks. One group of six mice were observed for any symptoms of toxicity or neurological complications including sluggishness, lack of grooming, hemiparesis, and weight loss on a daily basis for two months. A second group of six mice were sacrificed at two weeks, brains were removed and fixed in 10% neutral buffered formalin, and sections of brain tissue stained with hematoxylin and eosin.

ELISA 96-well plates were coated over night with synthetic polypeptide at a concentration of 600 ng/50 ul. Plates were dried and incubated at room temperature (RT) in blocking buffer (50 g Milk/L PBS) for 2 hrs. Rabbit antisera was diluted in PBS, added to plate, and incubated for 2 hours at room temperature. The presence of Claudin-7 pAb was visualized using anti-rabbit secondary antibody conjugated to horse radish peroxidase (HRP) at 490 nm.

Generation of Claudin-7 Polyclonal Antibody

Anti-human Claudin-7 pAb was raised in rabbits against the synthetic polypeptide (CKAGYRAPRSYPKSNSS-KEYV) (SEQ ID NO. 1) (Mimotopes), which corresponds to the C-terminus of human Claudin-7. The presence of Claudin-7-polyclonal antibody in successive bleeds was determined by ELISA. 96-well plates were coated over night with synthetic polypeptide at a concentration of 600 ng/50 µl. Plates were dried and incubated at room temperature (RT) in blocking buffer (50 g Milk/L PBS) for 2 hrs. Rabbit antisera was diluted in PBS, added to plate, and incubated for 2 hours at RT. The presence of Claudin-7 pAb was visualized using anti-rabbit secondary antibody conjugated to horse radish peroxidase (HRP) at 490 nm.

Immunohistochemistry

Sections of human breast cancer tissue embedded in paraffin were obtained. Sections were deparaffinized in xylene and rehydrated through graded EtOH. Antigen retrieval was performed by microwaving sections in 0.01M Citrate buffer, pH 6.0 for 20 min. Sections were cooled for 1 hour and then immersed in 0.3% $H_2O_2$ in MeOH to quench endogenous peroxidase activity for 30 min. Blocking was performed in diluted normal blocking serum (Vectastain kit, Vector Labs). Sections were probed using Claudin-3 and 4 antibody, followed by biotinylated secondary antibody (Vectastain kit, Vector Labs), incubation with ABC reagent (Vectastain kit, Vector Labs), and DAB (Vector kit, Vector Labs). Finally, sections were counterstained in Hematoxylin, dehydrated, cleared in xylene, and visualized by light microscopy.

RT-PCR

Total RNA was extracted using Trizol per instructions (Sigma Co, St. Louis, Mo.). cDNA was generated by reverse transcription. Reactions contained 2 µg DNAse-treated RNA, 0.25 µg/µl pdN6 random primers (Pharmacia), 1× first-strand buffer (Life Technologies), 1 mM of each deoxynucleotide triphosphate (Pharmacia), 200 units Superscript reverse transcriptase (Life Technologies), and were incubated for 1 hr at 37° C., followed by heat inactivation at 70° C. for 15 min. PCR was performed using the primers: 5'-CCACTCGAGC-CCTAATGGTG-3' (sense) (SEQ ID NO: 18) and 5' GGTAC-CCAGCCTTGCTCTCA-3'(anti-sense) (SEQ ID NO: 19) for Claudin-7. Coamplified products of 36B4, a "housekeeping" ribosomal protein gene, were used as an internal control, using primers 5'-GATTGGCTACCCAACTGTTGCA-3' (sense) (SEQ ID NO:20) and 5' AGGGGCAGCAGCCA-CAAAGGC-3' (anti-sense) (SEQ ID NO: 21). The 25 µl reactions contained 1× buffer (2× reaction mix, BRL), 1 µl cDNA, and 100 nm of each primer. The PCR conditions were: 1 cycle of 94° C. for 1 min, "hot start," followed by addition of 1 unit of Taq polymerase (RedTaq, Sigma), 35 cycles of 94° C. for 30 sec, 59° C. for 30 sec, 72° C. for 45 sec, and finally 1 cycle of 72° C. for 5 min. PCR samples were resolved by electrophoresis on a 1.5% agarose gel.

Western Blotting

Primary breast cancer tissue, normal, and benign (B) mammary organoid tissue was homogenized. Total protein was extracted from tissue and cells using lysis buffer consisting of 15% glycerol, 5% SDS, and 250 mM Tris-HCl, pH 6.7. Equal amounts of protein from cell lysates were resolved using 12% SDS-PAGE (Invitrogen). Protein was then transferred to ECL nitrocellulose membranes (Amersham). Following Western transfer, membranes were probed with Claudin-3 and 4 (Zymed) and Actin (Amersham) antibodies, and developed using ECL (Amersham).

Example 8

Expression of Claudins 3 and 4 Protein in Primary Breast Carcinomas, Breast Cancer Cell Lines, and Normal Mammary Epithelium The expression of Claudin 3 and 4 proteins in primary breast carcinomas, breast cancer cell lines, and normal mammary organoids was determined by Western blot analysis. We found Claudin 3 and 4 proteins to be expressed in the majority of breast cancer cell lines (7/10) and, more importantly, in all primary breast tumors tested (15/15). Further, Claudin 3 and 4 proteins were over-expressed by more than 2-fold in 12/15 (p=0.008) and 5/15 (p=0.046) primary breast tumors, respectively, relative to human mammary epithelial cells and normal epithelial organoids obtained from reduction mammoplasty specimens as determined by densitometric scanning.

These results showed that primary breast carcinomas consistently express the receptors for CPE, Claudins 3 and 4, and have increased expression relative to normal mammary epithelial cells.

Although Western analysis showed expression of Claudins 3 and 4 in all primary breast carcinomas tested it was important to determine the cellular localization of Claudins 3 and 4 as CPE-mediated cytolysis requires expression of its receptors at the cell membrane. Immunohistochemical analysis of Claudin 3 and 4 expression was performed on 10 primary breast carcinoma cases, 4 of which were included in our Western blot analysis. It was found that Claudin 3 and 4 proteins were both expressed at the cell membrane although some amount of cytoplasmic staining was also observed. Consistent with Western blot analysis, expression of Claudin 3 and 4 proteins in tumor epithelium was increased in 5/10 and 3/10 cases, respectively, relative to that seen in adjacent normal mammary epithelium.

Example 9

CPE Specifically and Efficiently Lyses Claudin 3 and 4 Expressing Breast Cancer Cells As CPE is known to efficiently destroy cells bearing Claudin 3 and/or 4 the ability of CPE to destroy several breast cancer cell lines was tested. Cells were plated at $3 \times 10^5$ cells/well in 6-well plates and grown to 80% confluence. Media was then removed and replaced with fresh media with or without recombinant CPE at concentrations ranging from 0.05 to 2 µg/ml. Cells were incubated at 37° C. for 60 min. Floating and attached cells were collected and counted using a hemocytometer. Cell viability was determined by trypan blue (0.4%) dye exclusion. Data from representative experiments are expressed as % cytotoxicity as compared to media control±S.D. Treatment of breast cancer cell lines with various concentrations of CPE resulted in rapid and dose-dependent cytolysis specific for cells expressing Claudins 3 and 4

Figure 3B:
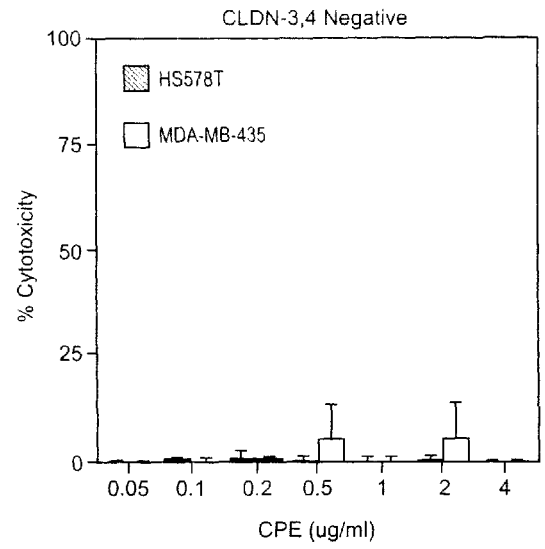

(FIG. 3). Treatment with CPE at a concentration of 1 ug/ml resulted in maximum cytolysis killing virtually 100% of the cells.

Example 10

Treatment of T47D Breast Cancer Cell Xenografts with CPE

Figure 4A:
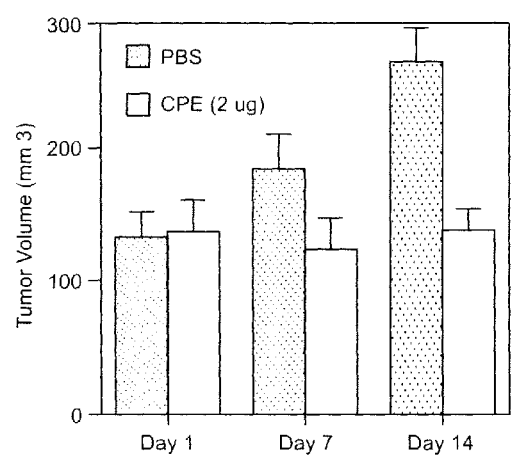
Figure 4B:
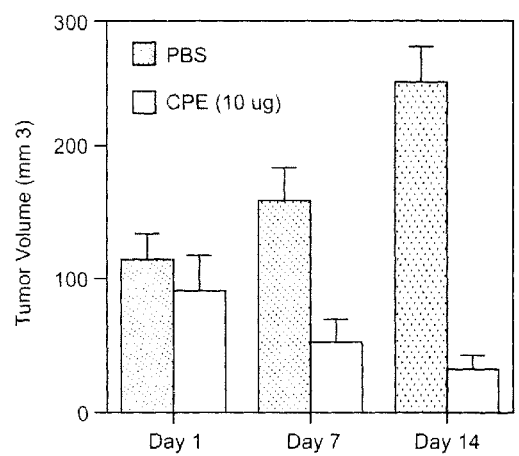

T47D cells ($1\times10^7$) were resuspended in matrigel and subcutaneously injected bilaterally in the flank of 6-8 week old SCID mice. Tumors were grown to approximately 100 mm$^3$ prior to CPE treatment. Tumors treated with recombinant CPE showed a significant dose-dependent reduction in tumor volume (FIG. 4). Further, Hematoxylin and Eosin staining of CPE-treated tumors revealed high levels of tumor necrosis accounting for approximately 30-80% of the total tumor area.

This example demonstrates that CPE effectively destroys Claudin 3 and 4 positive breast cancer cell lines established as xenografts in vivo.

Example 11

Expression of Claudin 3 and 4 in rat NMU-induced Breast Cancer Cell Lines

We next wanted to determine the effectiveness of recombinant CPE against spontaneously occurring breast tumors. To accomplish this we choose to use the Sprague-Dawley rat NMU-induced model of breast cancer. To determine if the cells from these tumors would be susceptible to CPE we first determined the expression of Claudin 3 and 4 proteins in two breast cancer cell lines established from these tumors by Western analysis. We found that both NMU 36 and NMU 58 breast cancer cell lines expressed Claudins 3 and 4, although NMU 36 expressed lower levels.

Example 12

Figure 5:
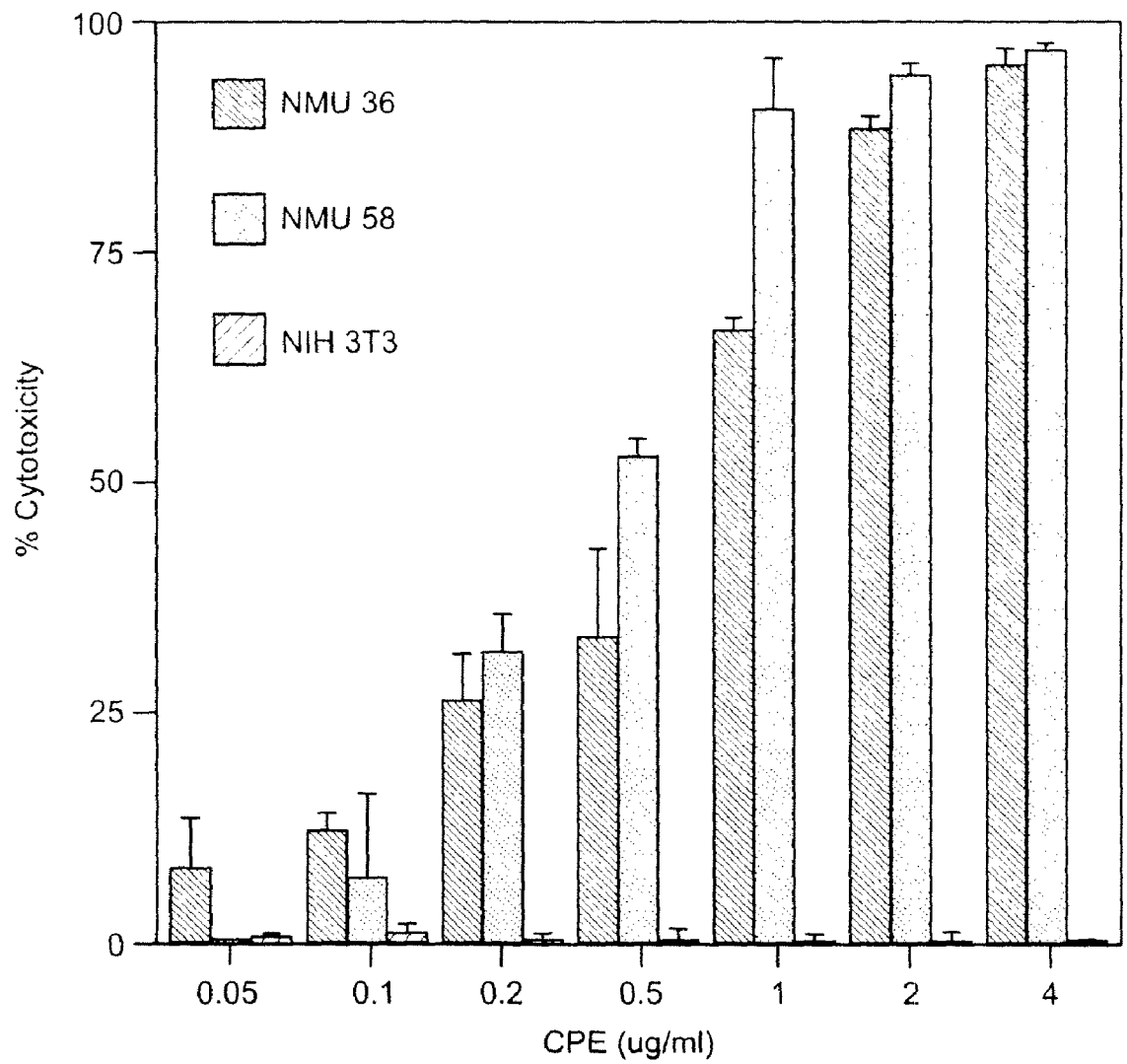

CPE Specifically and Efficiently Lyses Claudin 3 and 4 Expressing Rat Breast Cancer Cells To determine whether rat NMU-induced breast cancer cell lines were sensitive to the cytolytic effects of recombinant CPE we treated NMU 36 and NMU 58 with various concentrations of CPE for a period of 60 min (FIG. 5). Consistent with our results in human breast cancer cell lines, CPE treatment resulted in rapid and dose-dependent cytolysis specific for cells expressing claudins 3 and 4 as the claudin 3 and 4 negative NIH3T3 cells were unaffected. Further, NMU-36 cells were not as sensitive to CPE-mediated cytolysis as NMU 58, consistent with their lower level of claudin 3 and 4 expression. Despite their reduced sensitivity, virtually 100% cytolysis of NMU 36 cells was achieved at higher CPE concentrations.

Example 13

Figure 6A:
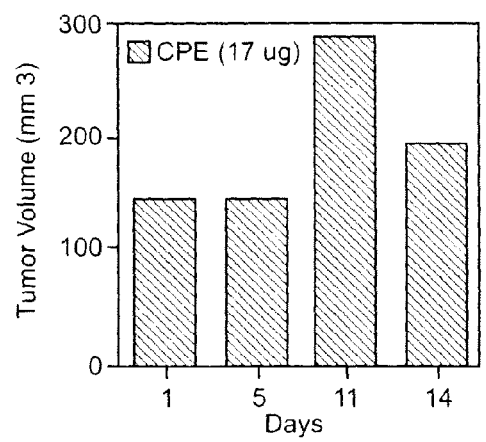
Figure 6B:
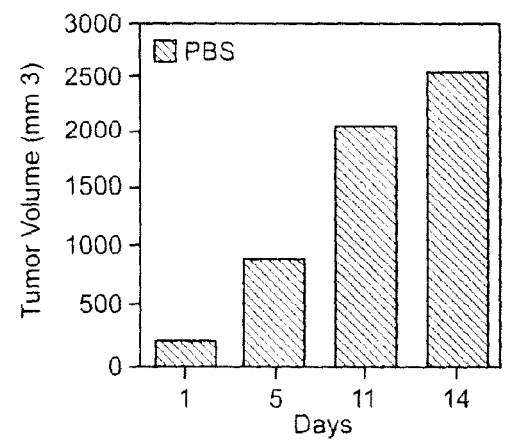
Figure 6C:
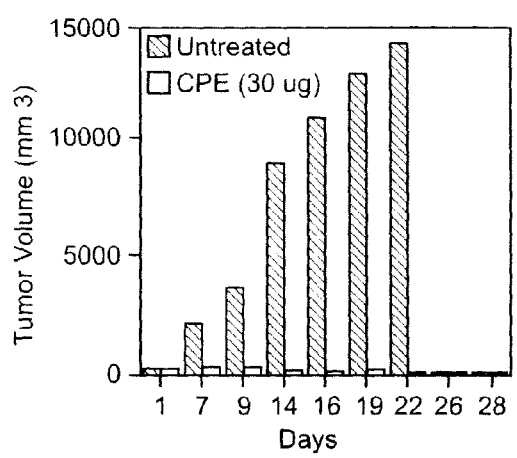
Figure 6D:
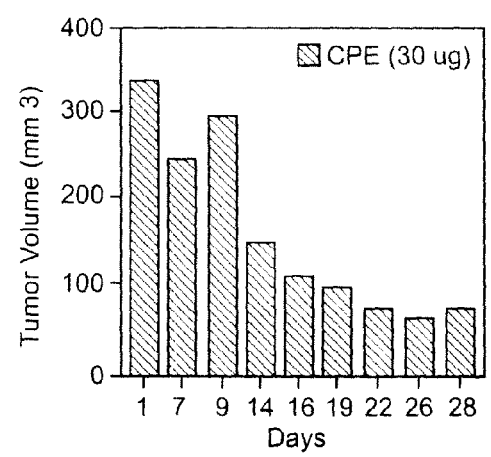
Figure 7:
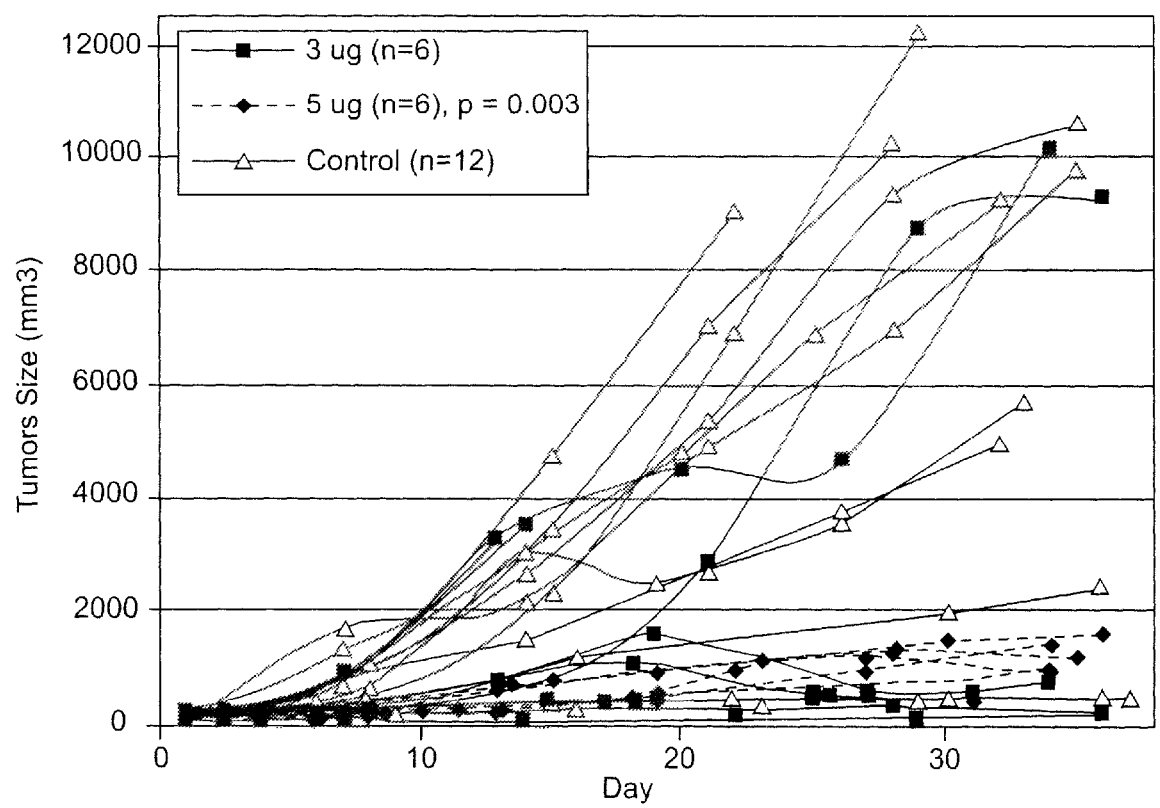
Figure 8:
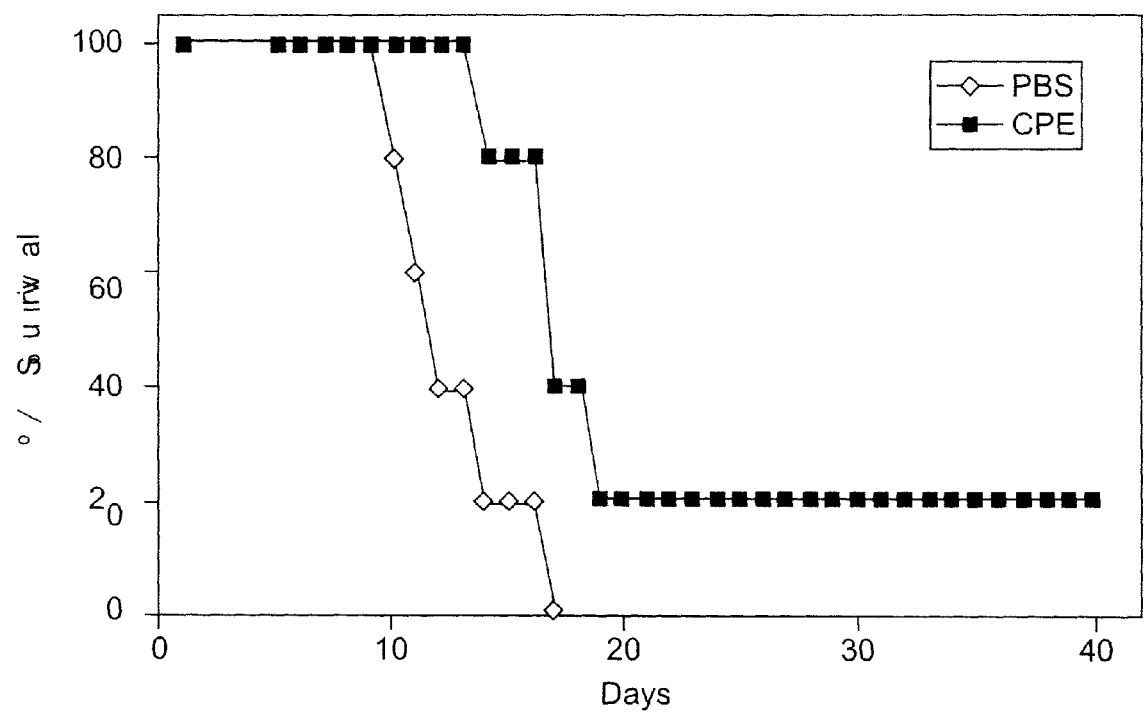

CPE Treatment of Sprague-Dawley NMU-Induced Breast Tumor by Intraductal Injection We further tested the therapeutic potential of CPE against breast cancer in the Sprague-Dawley NMU-induced model of breast cancer. Because numerous tissues in the body express claudins 3 and 4, systemic administration of CPE by routes such as intravenous, intramuscular, and oral may result in high systemic toxicity and greatly limit therapeutic efficacy. Therefore, the anti-tumor potential of CPE in vivo was tested using a novel intraductal (ID) administration approach (U.S. Pat. No. 6,330,472 to Sukumar et al., issued Dec. 11, 2001) through the test in order to limit systemic toxicity and provide more direct access of CPE to the tumor thereby increasing therapeutic efficacy. At 3-6 weeks of age, female Sprague-Dawley rats were injected with 50 mg/kg NMU i.p. Mammary tumors developed within several months. CPE was administered ID at various concentrations once tumors grew to a size of 100 mm$^3$. Three injections of 17 ug CPE over the course of 2 weeks prevented tumor growth (FIG. 6a) while an untreated tumor in the same animal grew to approximately 12.5 times the size (FIG. 6b). Increasing the concentration of CPE to 30 ug per injection while delivering 8 injections over the course of 4 weeks resulted in a reduction in tumor volume (FIGS. 6c,d). Concurrently, an untreated tumor in the same animal grew to more than 100 times the size. Further, CPE treatment led to significant tumor necrosis as evidenced by histological examination following Hematoxylin and Eosin staining. This experiment was subsequently repeated using native CPE, which has 10-fold higher activity that the recombinant CPE used previously. CPE was administered ID at 3 or 5 µg per injection once every three days for 30 days beginning once tumors reached a size of 100 mm3. Treatment with 5 µg CPE significantly inhibited the growth of tumors relative to untreated controls (FIG. 7). Although CPE administration of doses used in this experiment given i.p. are known to elicit system toxicity, no evidence of adverse reaction was observed in any of the treated animals. This example demonstrates that ID administration of CPE results in cytolysis of rat mammary tumors concurrent with a reduction in tumor volume without any evidence of systemic toxicity.

Example 14

Treatment of Metastatic Epithelial Cancers

Patients afflicted with cancer frequently die from metastasis to vital organs. Breast, lung, colon, kidney, and skin cancer patients frequently die from neurological complications resulting from metastases to the brain or bone. Other carcinomas have been reported to metastasize to the brain and bone as well, including those of prostate, pancreas, etc. Breast, lung, colon, kidney, prostate, and pancreas cancer cells all express claudins 3 and 4 whereas the cell types of the brain and bone do not. Thus, intracranial and intraosteal administration of CPE is used to eliminate cancer cells or metastatic tumors expressing claudin 3 and/or 4 while leaving brain or bone cells unharmed. In other words, targeting claudins 3 and 4 with CPE may provide a means of eliminating these metastases from the brain without damaging the brain itself. For example, in a case of breast cancer metastasis to the brain, a stereotactic injection of purified full-length CPE is administered directly to the site of the tumor. Injection is made through a small opening in the skull and guided with the aid of imaging equipment (e.g. CT scan, etc.). Tumor volume is measured via imaging (e.g. CT scan, PET scan, etc.) and repeated injections are administered as needed. Similarly, a micropump or CPE-saturated wafer may be implanted for slow drug release at the tumor site.

By immunohistochemical analysis, we found that claudin 3 and/or 4 were expressed in brain metastases from various primary tumors including those of breast (9/9), lung (7/7), colon (3/4), ovarian (1/2), and prostate (1/1). In contrast, sections of normal brain tissue obtained from hemispherectomy was negative for claudin 3 and 4 expression. To further explore the expression of CLDN 3 and 4 in brain cells we obtained a culture of primary human astrocytes. As determined by Western blot analysis, normal human astrocytes showed no expression of CLDN 3 or 4. Correspondingly, we found that these cells were unaffected by CPE treatment in vitro.

We next tested the toxicity of CPE to the brain using athymic nude and Balb/C mice.

Mice were administered doses of CPE ranging from 0.05-10 ug three days a week for two weeks by direct intracranial injection 2 mm posterior to the coronal suture and 2 mm lateral to the sagittal suture. The maximum tolerated dose of CPE was 0.5 ug native toxin. One group of mice were observed for a period of two months for any signs of illness or neurological complications including sluggishness, lack of grooming, huddling, weight loss, and hemiparesis. A second group of mice were sacrificed at two weeks, brains were removed, and sections of brain tissue stained with hematoxylin and eosin were analyzed by a neuropathologist. Mice treated with 0.5 ug CPE did not show any signs of toxicity or neurological damage as determined by daily observation or analysis of brain tissue sections.

Next, a mouse model of human breast cancer metastasis to the brain in athymic nude mice was generated. The injection of 250,000 MDA-MB-468 cells intracranially 2 mm posterior to the coronal suture and 2 mm lateral to the sagittal suture resulted in death at 18 days on average. Using this model, the efficacy of CPE in the treatment of breast cancer metastasis to the brain was tested. MDA-MB-468 breast cancer cells were injected into the brains of athymic nude mice. Following solid tumor formation, mice received intracranial injections of 0.5 ug CPE or PBS three times per week for 2 weeks. Mice were observed on a daily basis for signs of neurological complication resulting from tumor burden and were sacrificed when moribund. Mice receiving PBS began to show signs of excessive tumor burden on day 10 and did not survive beyond day 17. Mice that received CPE did not begin to show signs of illness until day 14 and 20% of mice survived beyond 40 days (FIG. 8). Thus, intracranial administration of CPE eliminated or delayed the growth of brain metastases.

Example 15

Development of Variant Forms of CPE for Use in Breast Cancer Treatment

Using PCR, a CPE cDNA molecule encoding all but the N-terminal 45 amino acids of CPE is generated. This variant is known to exhibit twice the cytotoxicity of full-length CPE and is tested in all studies previously using full-length CPE as outlined in previous examples.

CPE or a variant of CPE is conjugated to a linker rendering it unable to lyse cells expressing claudin 3 and/or 4 until the linker is enzymatically cleaved. The inactivation takes place by preventing binding to claudin 3 and/or 4, preventing cytotoxic activity following receptor binding, etc. The linker contains a sequence cleaved by a protease (e.g. matrix metalloproteases, serine proteases, etc.) that is over-expressed by tumors expressing Claudin 3 and/or 4 (including, but not limited to breast, lung, prostate, kidney, pancreas, etc.), tumor stromal elements, or tumor vasculature. This system of activation allows systemic administration of CPE and specific targeting of cancer cells while preventing systemic toxicity.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method for diagnosing metastatic breast, colon or lung cancer in a patient in need thereof, comprising the steps of
    determining a level of expression of claudin 3 or claudin 4 or both claudins 3 and 4 in cells obtained from brain or bone tissue from said patient, and
    assessing whether claudin 3 or claudin 4 or both claudins 3 and 4 are expressed in said cells at a level that is higher than a level of expression in disease-free individuals, wherein metastasis to brain or bone tissue is implicated when claudin 3 or claudin 4 or both claudins 3 and 4 are expressed at or above said level that is higher than a level of expression in disease-free individuals.

2. The method of claim 1, wherein said step of determining is carried out by exposing said cells to at least one antibody recognizing claudin 3 or claudin 4 or both claudin 3 and claudin 4.

3. The method of claim 1, wherein said tissue is a brain or bone biopsy tissue sample.

* * * * *

SEQUENCE LISTING

```
<160> NUMBER OF SEQ ID NOS: 21

<210> SEQ ID NO 1
<211> LENGTH: 21
<212> TYPE: PRT
<213> ORGANISM: Artificial
<220> FEATURE:
<223> OTHER INFORMATION: synthetic polypeptide

<400> SEQUENCE: 1

Cys Lys Ala Gly Tyr Arg Ala Pro Arg Ser Tyr Pro Lys Ser Asn Ser
1               5                   10                  15

Ser Lys Glu Tyr Val
            20

<210> SEQ ID NO 2
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 2
tggggaaagg gtggtgttg                                                    19

<210> SEQ ID NO 3
<211> LENGTH: 21
```

<212> TYPE: DNA
<213> ORGANISM: Artificial
<220> FEATURE:
<223> OTHER INFORMATION: synthetic oligonucleotide primer

<400> SEQUENCE: 3
ttacccaatt ttaaccacca c                                              21

<210> SEQ ID NO 4
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 4
gacgttaggt tattttcggt c                                              21

<210> SEQ ID NO 5
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 5
aaacgcgttt ctaaacgccg                                                20

<210> SEQ ID NO 6
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 6
ccactcgagc cctaatggtg                                                20

<210> SEQ ID NO 7
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 7
ggtacccagc cttgctctca                                                20

<210> SEQ ID NO 8
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 8
gattggctac ccaactgttg ca                                             22

<210> SEQ ID NO 9
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 9 cagggggcagc agccacaaag gc                                            22

<210> SEQ ID NO 10
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 10
aaatgtaaga aggcccgtat agc                                            23

<210> SEQ ID NO 11
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 11
gctaccaagg cggcaagac                                                 19

<210> SEQ ID NO 12
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 12
ccacgatgaa aattatgcct ccaccca                                        27

<210> SEQ ID NO 13
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 13
cccatgttcg tcatgggtgt                                                20

<210> SEQ ID NO 14
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 14
tggtcatgag tccttccacg ata                                            23

<210> SEQ ID NO 15
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 15
ctgcaccacc aactgcttag                                                20

<210> SEQ ID NO 16
<211> LENGTH: 19
<212> TYPE: DNA
<213> ORGANISM: Artificial
<220> FEATURE:
<223> OTHER INFORMATION: synthetic oligonucleotide primer

```
<400> SEQUENCE: 16
gtgattttgg tgtttaggt                                                  19

<210> SEQ ID NO 17
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 17
atcccaaaat atcctaaact a                                               21

<210> SEQ ID NO 18
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 18
ccactcgagc cctaatggtg                                                 20

<210> SEQ ID NO 19
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 19
ggtacccagc cttgctctca                                                 20

<210> SEQ ID NO 20
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 20
gattggctac ccaactgttg ca                                              22

<210> SEQ ID NO 21
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 21
aggggcagca gccacaaagg c                                               21
```